United States Patent
Cartt et al.

(10) Patent No.: US 9,550,822 B2
(45) Date of Patent: *Jan. 24, 2017

(54) ACTH PROPHYLACTIC TREATMENT OF RENAL DISORDERS

(71) Applicants: Questcor Pharmaceuticals, Inc., Hayward, CA (US); Rhode Island Hospital, Providence, RI (US)

(72) Inventors: Steve Cartt, Hayward, CA (US); Rujun Gong, Providence, RI (US)

(73) Assignees: QUESTCOR PHARMACEUTICALS, INC., Hayward, CA (US); RHODE ISLAND HOSPITAL, Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/313,903

(22) Filed: Jun. 24, 2014

(65) Prior Publication Data

US 2014/0336104 A1 Nov. 13, 2014

Related U.S. Application Data

(63) Continuation of application No. 13/281,175, filed on Oct. 25, 2011, now Pat. No. 8,796,416.

(60) Provisional application No. 61/406,550, filed on Oct. 25, 2010.

(51) Int. Cl.
| | |
|---|---|
| A61K 38/00 | (2006.01) |
| A61K 38/22 | (2006.01) |
| A61K 38/35 | (2006.01) |
| A61K 38/16 | (2006.01) |
| A61K 38/28 | (2006.01) |
| A61P 5/00 | (2006.01) |
| A61P 5/44 | (2006.01) |
| A61P 13/12 | (2006.01) |
| C07K 14/575 | (2006.01) |
| C07K 14/695 | (2006.01) |
| C07K 5/00 | (2006.01) |
| C07K 7/00 | (2006.01) |
| C07K 16/00 | (2006.01) |
| C07K 17/00 | (2006.01) |
| A61K 38/17 | (2006.01) |
| C07K 7/06 | (2006.01) |
| C07K 7/08 | (2006.01) |

(52) U.S. Cl.
CPC ............ *C07K 14/575* (2013.01); *A61K 38/16* (2013.01); *A61K 38/1709* (2013.01); *A61K 38/35* (2013.01); *C07K 7/06* (2013.01); *C07K 7/08* (2013.01); *C07K 14/695* (2013.01)

(58) Field of Classification Search
None
See application file for complete search history.

(56) References Cited

U.S. PATENT DOCUMENTS

| | | |
|---|---|---|
| 3,598,122 A | 8/1971 | Zaffaroni |
| 3,598,123 A | 8/1971 | Zaffaroni |
| 3,710,795 A | 1/1973 | Higuchi et al. |
| 3,731,683 A | 5/1973 | Zaffaroni |
| 3,742,951 A | 7/1973 | Zaffaroni |
| 3,814,097 A | 6/1974 | Ganderton et al. |
| 3,921,636 A | 11/1975 | Zaffaroni |
| 3,972,995 A | 8/1976 | Tsuk et al. |
| 3,993,072 A | 11/1976 | Zaffaroni |
| 3,993,073 A | 11/1976 | Zaffaroni |
| 3,996,934 A | 12/1976 | Zaffaroni |
| 4,031,894 A | 6/1977 | Urquhart et al. |
| 4,060,084 A | 11/1977 | Chandrasekaran et al. |
| 4,069,307 A | 1/1978 | Higuchi et al. |
| 4,077,407 A | 3/1978 | Theeuwes et al. |
| 4,201,211 A | 5/1980 | Chandrasekaran et al. |
| 4,229,447 A | 10/1980 | Porter |
| 4,230,105 A | 10/1980 | Harwood |
| 4,292,299 A | 9/1981 | Suzuki et al. |
| 4,292,303 A | 9/1981 | Keith et al. |
| 4,476,116 A | 10/1984 | Anik |
| 4,596,795 A | 6/1986 | Pitha |
| 4,755,386 A | 7/1988 | Hsiao et al. |
| 4,871,549 A | 10/1989 | Ueda et al. |
| 5,011,692 A | 4/1991 | Fujioka et al. |
| 5,017,381 A | 5/1991 | Maruyama et al. |
| 5,116,817 A | 5/1992 | Anik |
| 5,229,135 A | 7/1993 | Philippon et al. |
| 5,260,068 A | 11/1993 | Chen |
| 5,260,069 A | 11/1993 | Chen |
| 5,336,168 A | 8/1994 | Sibalis |
| 5,508,040 A | 4/1996 | Chen |
| 5,567,441 A | 10/1996 | Chen |
| 5,665,378 A | 9/1997 | Davis et al. |
| 5,739,136 A | 4/1998 | Ellinwood, Jr. et al. |
| 5,837,280 A | 11/1998 | Kenealy et al. |
| 5,837,284 A | 11/1998 | Mehta et al. |
| 5,840,329 A | 11/1998 | Bai |
| 5,858,401 A | 1/1999 | Bhalani et al. |
| 5,869,090 A | 2/1999 | Rosenbaum |
| 6,391,452 B1 | 5/2002 | Antonsen et al. |
| 6,667,048 B1 | 12/2003 | Lambert et al. |
| 6,923,983 B2 | 8/2005 | Morgan et al. |
| 6,929,801 B2 | 8/2005 | Klose et al. |
| 6,946,144 B1 | 9/2005 | Jordan |

(Continued)

FOREIGN PATENT DOCUMENTS

| | | |
|---|---|---|
| WO | WO-2009-040032 A2 | 4/2009 |
| WO | WO-2011-143152 A2 | 11/2011 |

OTHER PUBLICATIONS

NCBI Database, GenBank Accession No. 721746A, 1 page (1992).*

(Continued)

*Primary Examiner* — James H Alstrum Acevedo
*Assistant Examiner* — Thea D' Ambrosio
(74) *Attorney, Agent, or Firm* — Wilson Sonsini Goodrich & Rosati

(57) ABSTRACT

Provided herein are methods for prophylactic treatment of renal disorders comprising administration of adrenocorticotropic hormone (ACTH), or fragment, analog, complex or aggregate thereof, or any combination thereof, to an individual suspected of having, predisposed to, or at risk of developing a renal disorder.

13 Claims, No Drawings

(56) References Cited

U.S. PATENT DOCUMENTS

| | | | |
|---|---|---|---|
| 6,960,563 B2 | 11/2005 | Egbaria et al. | |
| 7,935,786 B2 | 5/2011 | Larsen | |
| 8,796,416 B1* | 8/2014 | Cartt et al. | 530/306 |
| 2002/0037832 A1* | 3/2002 | Nielsen et al. | 514/2 |
| 2007/0015257 A1 | 1/2007 | Hedley et al. | |
| 2009/0069242 A1 | 3/2009 | Jonassen et al. | |
| 2009/0130216 A1 | 5/2009 | Cartt et al. | |

OTHER PUBLICATIONS

Doi et al., J. Clin. Invest. 119: 2868-2878 (2009).*
Andreoli, Pediatr. Nephrol. 24:253-263 (2009).*
Doi, et al., Kidney Int. 73:1266-1274 (2008).*
Background on ACTHAR® at www.acthar.com/mspatient/how-acthar-works, 10 pages (accessed on Jul. 27, 2015).*
Kohda et al., Curr. Opin. Nephr. Hypertension 7:413-417 (1998).*
UniProt Database, Accession No. P01192, 11 pages (accessed on Apr. 19, 2016).*
Andreoli, S.P., "Acute kidney injury in children," Pediatr. Nephrol, 24:253-263 (2009).
Background information on ACTHAR [retrieved online] www.acthar.com/mspatient/how-acthar-works, 3 pages (accessed on Dec. 2012).
Bierowski et al., "Chronic renal failure and shortened lifespan in COL4A3+/-31 mice: an animal model for thin basement membrane nephropathy," J Am Soc Nephrology 2006, 17:1986-1994.
Chiou & Riegelman, "Pharmaceutical Application of Solid Dispersion Systems," Journal of Pharmaceuticals Sciences, vol. 60, No. 9, pp. 1281-1302 (1971).
Doi et al., "Animal models of sepsis and sepsis-induced kidney injury," J. Clin. Invest. 119:2868-2878 (2009).
Doi et al., "AP214, an analogue of a-melanocyte-stimulating hormone, ameliorates sepsis-induced acute kidney injury and mortality," *Kidney Int.*, Jun. 2008, 73(11): 1266-1274.
Karsi et al., "Linkage Mapping of the Channel Catfish *Proopiomelanocortin (POMC)* gene," International Society for Animal Genetics, 36 (169-190), pp. 171-173 (2005).
Lee et al., "On the Structure of Human Corticotropin (Adrenocorticotropic Hormone)," J. Biol. Chem 236:2970-2974 (1961).
Levey et al., "A new equation to estimate glomerular filtration rate," Annals of Internal Medicine 2009, 150:604-612.
Marti-Carvajal, et al., "Human recombinant activated protein C for severe sepsis," The Cochrane Collaboration, Issue 5, published by John Wiley & Sons, ltd., pp. 1-50 (2012).
NCBI Accession No. EU184858, (3007).
NCBI Accession No. K01877, (1993).
NCBI Accession No. NM_000939, (2013).
NCBI Accession No. NM_001035256, (2013).
NCBI Accession No. S73519, (1995).
NCBI Blast Alignment Search, vitamin K-dependent protein C preproprotein vs. ACTH 1-39, 3 pages (conducted on Nov. 30, 2012).
NCBI Database, Accession No. NP_000303, vitamin K-dependent protein C preproprotein, 8 pages (last updated 2012).
Togel et al., "Administered mesenchymal stem cells protect against ischemic acute renal failure through differentiation-independent mechanisms," 2005, Am J Physiol Renal Physiol 289:31-42.
U.S. Appl. No. 13/281,175 Office Action mailed Dec. 13, 2012.
U.S. Appl. No. 13/281,175 Office Action mailed Jun. 25, 2013.

\* cited by examiner

ACTH PROPHYLACTIC TREATMENT OF RENAL DISORDERS

CROSS REFERENCE

This patent application is a continuation application of U.S. patent application Ser. No. 13/281,175, filed Oct. 25, 2011, now U.S. Pat. No. 8,796,416, which claims benefit of U.S. Provisional Application No. 61/406,550 filed Oct. 25, 2010, each of which is incorporated by reference herein in its entirety.

BACKGROUND OF THE INVENTION

Renal disorders are a major health concern in the United States, with an estimated 11.5 percent of adults ages 20 or older in the U.S. having physiological evidence of a chronic kidney disease (Levey et al. *Annals of Internal Medicine* 2009, 150:604-612). Renal disorders include short-term disorders that may cause temporary changes in kidney function such as kidney infections, obstruction from kidney stones, sepsis, hypovolumia, trauma, and some medications; chronic disorders where impaired kidney function may be permanent; and total kidney failure. When the kidneys lose about ninety percent or more of their function, an individual is diagnosed with "end-stage renal disease (ESRD)."

SUMMARY OF THE INVENTION

Described herein are methods of prophylactic treatment of renal disorders comprising administration of adrenocorticotropic hormone (ACTH), or ACTH-like compound, composition and/or preparation to an individual in need thereof. In some instances, administration of ACTH protects against loss of renal function or impairment. In other instances, administration of ACTH delays the onset of a renal disorder. In other instances, administration of ACTH reduces the incidence or likelihood of a renal disorder. In further instances, administration of ACTH reduces the extent of damage or deterioration of a renal disorder. In other embodiments, upon detection of a biomarker described herein, the methods of treatment described herein allow for prophylactic administration of ACTH in individuals who are predisposed to a renal disorder. In further embodiments methods described herein improve an impaired kidney function associated with a renal disorder.

Accordingly, in one aspect provided herein is a method of prophylactically treating a renal disorder in an individual comprising selecting an individual suspected of having, predisposed to, or at risk of developing a renal disorder and administering adrenocorticotropic hormone (ACTH) peptide, or fragment, analog, complex or aggregate thereof, or any combination thereof, to the individual in need thereof, wherein the ACTH peptide or fragment, analog, complex or aggregate thereof, or any combination thereof, is administered as a first dose and one or more subsequent doses;

provided that the ACTH peptide or fragment, analog, complex or aggregate thereof, or any combination thereof, is not alpha-melanocyte stimulating hormone (alpha-MSH).

In a specific aspect, provided herein is a method of prophylactically treating acute kidney injury (AKI) (also known as acute renal failure (ARF)) in an individual in need thereof comprising selecting an individual suspected of having, predisposed to, or at risk of developing acute kidney injury and administering adrenocorticotropic hormone (ACTH) peptide to the individual, wherein the ACTH peptide is administered as a first dose and one or more subsequent doses.

In certain embodiments, the renal disorder is chronic kidney disease. In other embodiments, the renal disorder is acute kidney injury.

In some of the embodiments of the methods described herein, the individual has sepsis or is undergoing surgery. In other embodiments of the methods described herein, the selection of an individual for prophylactic treatment is based upon a change in a kidney biomarker in the individual as compared to a normal baseline level of the kidney biomarker in the general population.

In certain embodiments, the selection of an individual is based upon a decrease in glomerular filtration rate (GFR) as compared to a normal baseline level. In other embodiments, the selection of an individual is based upon an increase in serum creatinine as compared to a normal baseline level. In other embodiments, the selection of an individual is based upon an increase in urinary protein as compared to a normal baseline level. In other embodiments, the selection of an individual is based upon an elevated asymmetric dimethyl-arginine (ADMA) as compared to a normal baseline level. In other embodiments, the selection of an individual is based upon an elevated cystatin C (CysC) as compared to a normal baseline level. In other embodiments, the selection of an individual is based upon an elevated C-reactive Protein (CRP) as compared to a normal baseline level. In other embodiments, the selection of an individual is based upon an elevated soluble tumor necrosis factor receptor II (sTNFrii) as compared to a normal baseline level. In further embodiments, selection of an individual is based upon detection of urinary neutrophil gelatinase-associated lipocalin (NGAL). In further embodiments, selection of an individual is based upon detection of urinary interleukin-18 (IL-18). In further embodiments, selection of an individual is based upon detection of urinary kidney injury molecule-1 (KIM-1). In additional embodiments, selection of an individual is based upon decreased urine output.

Also provided herein is a method of treating renal damage caused by ischemia to the kidney in an individual in need thereof comprising administering adrenocorticotropic hormone (ACTH) peptide or fragment, analog, complex or aggregate thereof, or any combination thereof, to the individual in need thereof, wherein the ACTH peptide or fragment, analog, complex or aggregate thereof, or any combination thereof, is administered as a first dose and one or more subsequent doses;

provided that the ACTH peptide or fragment, analog, complex or aggregate thereof, or any combination thereof, is not alpha-melanocyte stimulating hormone (alpha-MSH).

In certain embodiments, the renal damage caused by ischemia to the kidney is renal shock. In certain embodiments, the renal damage caused by ischemia to the kidney is AKI.

In some embodiments of the methods described above, the ACTH peptide or fragment, analog, complex or aggregate thereof, or any combination thereof, is a ACTH peptide. In some embodiments, the ACTH peptide is $ACTH_{1-39}$ peptide having the formula(SEQ ID NO: 1):

```
H-Ser-Tyr-Ser-Met-Glu-His-Phe-Arg-Trp-Gly-
  1   2   3   4   5   6   7   8   9   10

Lys-Pro-Val-Gly-Lys-Lys-Arg-Arg-Pro-Val-
 11  12  13  14  15  16  17  18  19  20
```

```
Lys-Val-Try-Pro-Asp-Gly-Ala-Glu-Asp-Gln-
 21  22  23  24  25  26  27  28  29  30

Leu-Ala-Glu-Ala-Phe-Pro-Leu-Glu-Phe-OH
 31  32  33  34  35  36  37  38  39.
```

In some embodiments, the ACTH peptide is $ACTH_{1-39}$ peptide having the formula (SEQ ID NO. 1):

```
H-Ser-Tyr-Ser-Met-Glu-His-Phe-Arg-Trp-Gly-
  1   2   3   4   5   6   7   8   9  10

Lys-Pro-Val-Gly-Lys-Lys-Arg-Arg-Pro-Val-
 11  12  13  14  15  16  17  18  19  20

Lys-Val-Try-Pro-Asp-Gly-Ala-Glu-Asp-Gln-
 21  22  23  24  25  26  27  28  29  30

Leu-Ala-Glu-Ala-Phe-Pro-Leu-Glu-Phe-OH
 31  32  33  34  35  36  37  38  39.
``` or a complex, aggregate, or analog thereof, or any combination thereof.

In some embodiments of the methods described herein, the ACTH peptide is $ACTH_{1-24}$ peptide having the formula (SEQ ID NO. 2):

```
H-Ser-Tyr-Ser-Met-Glu-His-Phe-Arg-Trp-Gly-
  1   2   3   4   5   6   7   8   9  10

Lys-Pro-Val-Gly-Lys-Lys-Arg-Arg-Pro-Val-
 11  12  13  14  15  16  17  18  19  20

Lys-Val-Try-Pro
 21  22  23  24
``` or a complex, aggregate, or analog thereof, or any combination thereof.

In some embodiments of the methods described herein, the ACTH peptide is $ACTH_{1-17}$ peptide having the formula (SEQ ID NO. 3):

```
H-Ser-Tyr-Ser-Met-Glu-His-Phe-Arg-Trp-Gly-
  1   2   3   4   5   6   7   8   9  10

Lys-Pro-Val-Gly-Lys-Lys-Arg-
 11  12  13  14  15  16  17
``` or a complex, aggregate, or analog thereof, or any combination thereof.

In some embodiments of the methods described herein, the ACTH peptide is $ACTH_{4-10}$ peptide of formula (SEQ ID NO. 4):

```
Met-Glu-His-Phe-Arg-Trp-Gly
 4   5   6   7   8   9  10
``` or a complex, aggregate, or analog thereof, or any combination thereof.

In some embodiments of the methods described herein, the ACTH peptide is $ACTH_{4-9}$ peptide analog of formula (SEQ ID NO. 5):

```
Met-Glu-His-Phe-D-Lys-Phe-OH
``` or a complex, aggregate, or analog thereof, or any combination thereof.

In some embodiments of the methods described herein, the ACTH peptide is a peptide of formula (SEQ ID NO. 6):

```
Ac-Ser-Tyr-Ser-Met-Glu-His-Phe-Arg-Trp-Gly-Lys-
Pro-Val
``` or a complex, aggregate, or analog thereof, or any combination thereof.

In some embodiments of the methods described herein, the ACTH peptide is a peptide of formula (SEQ ID NO. 6):

```
H-Ser-Tyr-Ser-Met-Glu-His-Phe-Arg-Trp-Gly-Lys-
Pro-Val
``` or a complex, aggregate, or analog thereof, or any combination thereof.

In some embodiments of the methods described herein, the ACTH peptide is a peptide of formula (SEQ ID NO. 7):

```
D-Ala-Gln-Tyr-Phe-Arg-Trp-Gly-NH_2.
``` or a complex, aggregate, or analog thereof, or any combination thereof.

In some embodiments of the methods described herein, the first dose of ACTH peptide or fragment, analog, complex or aggregate thereof, or any combination thereof, comprises a dose between about 10 IU and about 150 IU, and the one or more subsequent doses of ACTH peptide or fragment, analog, complex or aggregate thereof, or any combination thereof, is administered about every day, about every 2 days, about every 5 days, about every week, about every two weeks, about every three weeks, about every month, about every two months, or any combination thereof.

In some embodiments of the methods described herein, the first dose of ACTH peptide or fragment, analog, complex or aggregate thereof, or any combination thereof, comprises a dose between about 10 IU and about 150 IU, and the one or more subsequent doses of ACTH peptide or fragment, analog, complex or aggregate thereof, or any combination thereof, are between about 20%-80% of the first dose.

In some embodiments of the methods described herein, the first dose of ACTH peptide or fragment, analog, complex or aggregate thereof, or any combination thereof, comprises a first dose of between about 10 IU and about 150 IU, and the one or more subsequent doses of ACTH peptide or fragment, analog, complex or aggregate thereof, or any combination thereof, are between about 20%-60% of the first dose.

In some embodiments of the methods described herein, the intermittent dose of ACTH peptide or fragment, analog, complex or aggregate thereof, or any combination thereof, comprises a first dose of between about 10 IU and about 150 IU, and the one or more subsequent doses of ACTH peptide or fragment, analog, complex or aggregate thereof, or any combination thereof, are between about 10 IU and about 80 IU.

In some specific embodiments of the methods described herein, an individual in need thereof is administered $ACTH_{1-39}$ peptide, wherein the first dose of $ACTH_{1-39}$ peptide comprises a dose between about 10 IU and about 150 IU, and the one or more subsequent doses of $ACTH_{1-39}$ peptide is administered about every day, about every 2 days, about every 5 days, about every week, about every two weeks, about every three weeks, about every month, about every two months, or any combination thereof.

In some specific embodiments of the methods described herein, an individual in need thereof is administered $ACTH_{1-39}$ peptide, wherein the first dose of $ACTH_{1-39}$ peptide comprises a dose between about 10 IU and about 150 IU, and the one or more subsequent doses of $ACTH_{1-39}$ peptide are between about 20%-80% of the first dose.

In some specific embodiments of the methods described herein, an individual in need thereof is administered $ACTH_{1-39}$ peptide, wherein the first dose of $ACTH_{1-39}$ peptide comprises a first dose of between about 10 IU and about 150 IU, and the one or more subsequent doses of $ACTH_{1-39}$ peptide are between about 20%-60% of the first dose.

In some specific embodiments of the methods described herein, an individual in need thereof is administered $ACTH_{1-39}$ peptide, wherein the intermittent dose of $ACTH_{1-39}$ peptide comprises a first dose of between about 10 IU and about 150 IU, and the one or more subsequent doses of $ACTH_{1-39}$ peptide are between about 10 IU and about 80 IU.

In some embodiments of the methods described herein, the ACTH peptide or fragment, analog, complex or aggregate thereof, or any combination thereof, is administered to an individual in need thereof in an amount sufficient to provide plasma cortisol secretion levels between about 0.1 to about 4 times, or between about 1.1 to about 4 times the plasma cortisol secretion levels of a normal individual.

In some embodiments of the methods described herein, the ACTH peptide or fragment, analog, complex or aggregate thereof, or any combination thereof, is administered to an individual in need thereof in an amount sufficient to provide plasma cortisol secretion levels between about 0.1 to about 4 times, or between about 1.1 to about 4 times the plasma cortisol secretion levels of the individual prior to administration of the ACTH peptide or fragment, analog, complex or aggregate thereof, or any combination thereof.

In some specific embodiments of the methods described herein, an individual in need thereof is administered $ACTH_{1-39}$ peptide, wherein the $ACTH_{1-39}$ peptide is administered to the individual in need thereof in an amount sufficient to provide plasma cortisol secretion levels between about 0.1 to about 4 times, or between about 1.1 to about 4 times the plasma cortisol secretion levels of a normal individual.

In some specific embodiments of the methods described herein, an individual in need thereof is administered $ACTH_{1-39}$ peptide, wherein the $ACTH_{1-39}$ peptide is administered to the individual in need thereof in an amount sufficient to provide plasma cortisol secretion levels between about 0.1 to about 4 times, or between about 1.1 to about 4 times the plasma cortisol secretion levels of the individual prior to administration of the $ACTH_{1-39}$ peptide.

In some embodiments of the methods described herein, the ACTH peptide or fragment, analog, complex or aggregate thereof, or any combination thereof, is administered as an ACTH preparation. For example, in some embodiments, an ACTH preparation comprises ACTH peptide or fragment, analog, complex or aggregate thereof, or any combination thereof, and any other proteins and/or other substances that are present in a homogenized pituitary extract obtained from an appropriate animal source (e.g., a pig pituitary extract). In some specific embodiments of the methods described herein, an individual in need thereof is administered an $ACTH_{1-39}$ peptide which is administered as an $ACTH_{1-39}$ preparation.

In some embodiments, the ACTH peptide or fragment, analog, complex or aggregate thereof, or any combination thereof, is administered as a prodrug. In some specific embodiments of the methods described herein, an individual in need thereof is administered an $ACTH_{1-39}$ peptide which is administered as a prodrug. In some embodiments, the $ACTH_{1-39}$ peptide or fragment, analog, complex or aggregate thereof, or any combination thereof, is administered as a prolonged release formulation. In some specific embodiments of the methods described herein, an individual in need thereof is administered an $ACTH_{1-39}$ peptide which is administered as a prolonged release formulation.

In some embodiments, the ACTH peptide or fragment, analog, complex or aggregate thereof, or any combination thereof, is administered intramuscularly. In some embodiments, the ACTH peptide or fragment, analog, complex or aggregate thereof, or any combination thereof, is administered subcutaneously.

In some embodiments, the ACTH peptide or fragment, analog, complex or aggregate thereof, or any combination thereof, is administered intravenously. In some embodiments, the ACTH peptide or fragment, analog, complex or aggregate thereof, or any combination thereof, is administered intrathecally. In some specific embodiments of the methods described herein, an individual in need thereof is administered an $ACTH_{1-39}$ peptide which is administered intramuscularly, subcutaneously, intravenously or intrathecally.

In some embodiments, the ACTH peptide or fragment, analog, complex or aggregate thereof, or any combination thereof, is a porcine ACTH peptide or fragment, analog, complex or aggregate thereof, or any combination thereof. In some specific embodiments of the methods described herein, an individual in need thereof is administered an ACTH peptide which is a porcine ACTH peptide.

In some embodiments, the ACTH peptide or fragment, analog, complex or aggregate thereof, or any combination thereof, is a human ACTH peptide or fragment, analog, complex or aggregate thereof, or any combination thereof. In some specific embodiments of the methods described herein, an individual in need thereof is administered an ACTH peptide which is a human ACTH peptide. In some embodiments, the ACTH peptide or fragment, analog, complex or aggregate thereof, or any combination thereof, is a recombinant ACTH peptide or fragment, analog, complex or aggregate thereof, or any combination thereof. In some specific embodiments of the methods described herein, an individual in need thereof is administered an ACTH peptide which is a recombinant ACTH.

In additional embodiments, the methods described herein further comprise administration of a second therapeutic agent selected from an angiotensin-converting enzyme inhibitor, an angiotensin receptor blocker, a phosphate binder, hepatocyte growth factor (HGF), corticosteroids, erythropoietin, calcitriol, bardoxolone methyl, medoxomil, sulodexide and avosentan, wherein the second therapeutic agent is administered sequentially or simultaneously.

In another aspect provided herein is a method of reducing the likelihood of a renal disorder in an individual comprising selecting an individual suspected of having, predisposed to, or at risk of developing a renal disorder and administering of adrenocorticotropic hormone (ACTH) peptide, or fragment, analog, complex or aggregate thereof, or any combination thereof, to an individual in need thereof, wherein the ACTH peptide or fragment, analog, complex or aggregate thereof, or any combination thereof, is administered as a first dose and one or more subsequent doses.

In yet another aspect provided herein is a method of reducing the likelihood and severity of a renal disorder in an individual comprising selecting an individual suspected of having, predisposed to, or at risk of developing a renal disorder and administering $ACTH_{1-39}$ to an individual in need thereof, wherein the $ACTH_{1-39}$ is administered as a first dose and one or more subsequent doses.

In a further aspect, the methods described herein comprise treating an individual suspected of having, predisposed to, or at risk of developing a renal disorder comprising detecting a change in a kidney biomarker as compared to a normal baseline level of the kidney biomarker in the general population and administering adrenocorticotropic hormone (ACTH) peptide, or fragment, analog, complex or aggregate thereof, or any combination thereof, to an individual in need thereof, wherein the ACTH peptide or fragment, analog, complex or aggregate thereof, or any combination thereof, is administered as a first dose and one or more subsequent doses.

Also provided herein is a method of treating an individual suffering from acute kidney injury comprising administering adrenocorticotropic hormone (ACTH) peptide to the individual in need thereof, wherein the ACTH peptide is administered as a first dose and one or more subsequent doses. Also provided herein is a method of treating an individual suffering from acute kidney injury comprising administering $ACTH_{1-39}$ to the individual in need thereof, wherein the $ACTH_{1-39}$ is administered as a first dose and one or more subsequent doses.

In a further aspect, the methods described herein comprise treating an individual suspected of having, predisposed to, or at risk of developing a acute kidney injury comprising detecting a change in a kidney biomarker in the individual as compared to a normal baseline level of the kidney biomarker in the general population and administering adrenocorticotropic hormone (ACTH) peptide to the individual in need thereof, wherein the ACTH peptide is administered as a first dose and one or more subsequent doses.

For any of the methods describe above and herein, in one embodiment, the adrenocorticotropic hormone (ACTH) peptide, or fragment, analog, complex or aggregate thereof, or any combination thereof, is ACTH peptide. In some of such embodiments, the ACTH peptide is $ACTH_{1-39}$ peptide as described herein. In some of such embodiments, the ACTH peptide is $ACTH_{1-24}$ peptide as described herein. In some of such embodiments, the ACTH peptide is $ACTH_{1-17}$ peptide as described herein. In some of such embodiments, the ACTH peptide is $ACTH_{4-10}$ peptide as described herein. In some of such embodiments, the ACTH peptide is $ACTH_{4-9}$ peptide analog as described herein. In some of such embodiments, the ACTH peptide is any $ACTH_{1-39}$ fragment, or analog, complex, or aggregate thereof, as described herein, provided that the $ACTH_{1-39}$ fragment, or analog, complex, or aggregate thereof is not alpha-MSH or analog thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Provided herein, in some embodiments, are methods of prophylactical treatment of renal disorders comprising administration of ACTH to an individual in need thereof. A renal disorder is a disease or condition of the kidney that generally relates to impaired kidney function. In some embodiments herein, "prophylactic treatment" refers to treatment before renal function has been impaired or affected by a renal disorder to delay the onset of a renal disorder. In some embodiments, "prophylactic treatment" refers to treatment before renal function has been impaired or affected by a renal disorder to reduce the likelihood or incidence of a renal disorder. In a non-limiting example, a subject at risk for acute kidney injury can be prophylactically treated according to the present methods prior to undergoing a surgical procedure. In other embodiments, "prophylactic treatment" refers a treatment before renal function has been impaired or affected by a renal disorder to reduce the extent of damage to renal function or further deterioration by the onset of a renal disorder. In further embodiments, "prophylactic treatment" refers to treatment after kidney function has been impaired or affected by a renal disorder to reduce the extent of damage to renal function or further deterioration.

ACTH is a hormone that is secreted by the pituitary gland and is a part of the hypothalamus-pituitary-adrenal (HPA) axis that maintains the stress response and homeostasis in the body. In some instances ACTH plays a role in renal function. Physiologically, the principal effects of ACTH are stimulation of the adrenal cortex with subsequent increased production of glucocorticosteroids and/or cortisol from the adrenal cortex. ACTH levels are tightly regulated in the body via a negative feedback loop wherein glucocorticosteroids suppress the release of corticotropin release hormone (CRH) from the pituitary and CRH-mediated release of ACTH. In some instances, cortisol helps restore homeostasis after stress. In some instances, changed patterns of serum cortisol levels are observed in connection with abnormal ACTH levels. In some instances, prolonged ACTH-mediated secretion of abnormal levels of cortisol (e.g., higher or lower levels of cortisol compared to cortisol levels in normal individuals) has detrimental effects. Thus, any perturbation in the levels of ACTH has profound physiological implications.

The treatment and prevention of renal disorders present unique challenges. In some instances, current treatment regimens are directed to alleviation of symptoms of renal disorders and improving quality of life for patients; however, such treatments lengthen survival only by a few months. In other cases, a renal disorder has been progressed to a point, either by rapid onset or undetected gradual onset where current treatment regimens are ineffective. Current treatment regimens do not address the unmet medical need for therapies that address the underlying etiology of renal disorders and/or delay the progression of the kidney impairment.

Advantageously, in some embodiments, the methods of treatment of renal disorders described herein comprise administration of adrenocorticotropic hormone (ACTH) to an individual in need thereof in doses and/or dosing regimens such that, for example, any dysregulation in the renal function is remedied or partially remedied, thereby alleviating the symptoms of renal disorders and/or delaying progressive degeneration associated with certain renal disorders. In some embodiments, the methods of treatment of renal disorders (e.g., AKI) described herein delay, reduce or reverse damage to the kidney, thereby allowing for long term survival of individuals suspected of having, predisposed to, or at risk of developing a renal disorder.

Renal Disorders

Renal or kidney disorders encompass a wide range of conditions and diseases that generally relate to inadequate clearance of metabolic waste products from the blood and abnormal concentrations of electrolytes in the blood. Renal disorders include short-term problems in kidney function that might not cause permanent damage such as some kidney infections and obstruction from kidney stones, sepsis, hypovolumia, trauma, and some medications, as well as more permanent impairment in kidney function such as chronic kidney disease (CKD), acute kidney injury (AKI) or acute renal failure (ARF) and end-stage renal disease (ESRD).

As used herein, "chronic renal injury", "chronic renal tubular cell injury", "progressive renal disease", "chronic renal failure" (CRF), "chronic renal disease" (CRD), "chronic kidney injury", as well as other synonymous phrases, are all "chronic kidney disease" (CKD). Chronic kidney disease includes any kidney condition, dysfunction or injury that: (a) occurs over a prolonged or gradual period of time (e.g., minimally weeks, months, years, or decades) during which the rate of change of the injury can vary, (b) manifests as a prolonged or gradual decrease of renal tubular cell function or glomerular filtration rate (GFR) during which the rate of change of the function or rate can vary, and/or (c) manifests as a prolonged or gradual worsening of renal tubular cell injury during which the rate of change of the injury can vary. Chronic kidney disease is distinct from any kidney condition, dysfunction or injury that is caused by a sudden or rapidly terminating event (e.g., occurring instantaneously, or over the course of seconds, minutes, hours, or days). CKD often is undetected for months or years due to the gradual and prolonged loss of kidney function.

It is contemplated that diabetes and hypertension are among the most important causes of chronic kidney disease, however CKD is also associated with other conditions such as lupus. Other causes of CKD reportedly include chronic infection, chronic inflammation, glomerulonephritides, vascular disease, interstitial nephritis, a drug (e.g., anticancer agent or other medicine), a toxin, trauma, a renal stone, congestive heart failure, nephropathy from sickle cell anemia and other blood dyscrasias, nephropathy related to hepatitis, HIV, parvovirus and BK virus (a human polyomavirus), cystic kidney disease, congenital malformation, obstruction, malignancy, kidney disease of indeterminate cause, membranous glomerulonephritis, membranoproliferative glomerulonephritis, focal glomerular sclerosis, minimal change disease, cryoglobulinemia, Anti-Neutrophil Cytoplasmic Antibody (ANCA)-positive vasculitis, ANCA-negative vasculitis, amyloidosis, multiple myeloma, light chain deposition disease, complications of kidney transplant, chronic rejection of a kidney transplant, chronic allograft nephropathy, and the chronic effect of immunosuppressives. Acute renal failure or acute kidney injury may also lead to chronic kidney disease. When an individual experiences one or more of the causes of CKD described herein, in some embodiments, that individual is suspected of having, predisposed to, or at risk of developing a renal disorder.

"Acute kidney injury" (AKI) or "acute renal failure" (ARF) is a sudden or rapid loss of kidney function. The renal loss usually spans about 48 hours or less and stems from either an injury or insult that causes a functional or structural change in the kidney. A common cause of AKI is decreased effective blood flow to the kidney which results in renal ischaemia and a functional disorder, depression of glomerular filtration rate (GFR), or both. Systemic causes include, low blood volume, low blood pressure, and heart failure. Other systemic causes include local changes to the blood vessels supplying the kidney such as renal artery stenosis and renal vein thrombosis. Surgical patients that require cross-clamping of the aorta or renal vessels experience AKI in as much as 30% of cases. Damage to the kidney itself can also cause AKI. Common causes of damage are glomerulonephritis, acute tubular necrosis (ATN), and acute interstitial nephritis (AIN). Urinary tract obstruction can also cause AKI and may be related to benign prostatic hyperplasia (BPH), kidney stones, obstructed urinary catheter, bladder stone, bladder, ureteral or renal malignancy. AKI is also a common effect of sepsis. Sepsis often leads to multi-organ dysfunction and the kidney is one of the organs frequently afflicted. AKI occurs in about 19% patients with moderate sepsis, 23% with severe sepsis and 51% with septic shock. Other causes of AKI include exposure to certain toxins, chemicals and drugs such NSAIDS, acetaminophen, cisplatin, rapamycin and radioconstrast media used in medical imaging. When an individual experiences one or more of the causes of AKI described herein, in some embodiments, that individual is suspected of having, predisposed to, or at risk of developing a renal disorder.

Renal damage or acute kidney injury has several causes including and not limited to (1) Prerenal—as an adaptive response to severe volume depletion and hypotension, with structurally intact nephrons; or (2) Intrinsic—in response to cytotoxic, ischemic, or inflammatory insults to the kidney, with structural and functional damage; or (3) Postrenal—from obstruction to the passage of urine. Accordingly, the methods provided herein include also include treatment of renal damage caused by ischemic or inflammatory insults to the kidney and/or renal shock and/or renal sepsis. In some of such embodiments, renal ischemia causes AKI.

Biomarkers for Renal Disorders

Markers have been identified that allow earlier identification and treatment of renal disorders as well as prevent progression of kidney diseases. In some embodiments of the methods described herein, selection of an individual suspected of having, predisposed to, or at risk of developing a renal disorder is through the use of biomarkers.

The glomerulus and the surrounding Bowman's capsule constitute the basic functional unit of the kidney. Glomerular filtration rate (GFR) is a standard measure of renal function. As a traditionally used biomarker, creatinine clearance is commonly used to measure GFR. Serum creatinine is commonly used as a surrogate measure of creatinine clearance. For instance, excessive levels of serum creatinine are generally accepted to indicate inadequate renal function and reductions in serum creatinine over time are accepted as an indication of improved renal function. Normal levels of creatinine in the blood are approximately 0.6 to 1.2 milligrams (mg) per deciliter (dl) in adult males and 0.5 to 1.1 milligrams per deciliter in adult females.

Urinary protein level measurement is another biomarker used to assess renal disorder. Renal tubules of the kidneys retain plasma proteins by reabsorption of such proteins as they pass through the glomerular filtration barrier. Normal urine protein excretion is up to 150 mg/dl. Therefore, the detection of excessive quantities or types of protein (proteinuria) in the urine is considered an early sign of significant renal or systemic disease.

Newer biomarkers have been identified that may have a use in early detection and/or prediction of renal disorders. Some examples of biomarkers include asymmetric dimethylarginine (ADMA), liver-type fatty acid-binding protein (L-FABP), cystatin C (CysC), C-reactive Protein (CRP), and soluble tumor necrosis factor receptor II (sTNFrii). Cystatin C and L-FABP are produced by cells outside the kidney and rely upon filtration across the glomerulus. ADMA is an endogenous nitric oxide synthase (NOS) inhibitor. Elevated levels have been shown to predict kidney disease progression rates. CRP and sTNFrii are measures of inflammatory activity. Their levels have been shown to correlate with kidney disease progression in inflamed states. CRP appears to correlate with endothelial injury, while sTNFrii has been associated with glomerular injury.

Other examples of biomarkers include neutrophil gelatinase-associated lipocalin (NGAL), interleukin-18 (IL-18) and kidney injury molecule-1 (KIM-1). Kidney NGAL is produced by the nephron in response to tubular epithelial damage and is a marker of tubulointerstitial (TI) injury. In AKI stemming from ischemia or nephrotoxicity, NGAL levels rise in the urine of subjects, after mild "subclinical" renal ischemia, in spite of normal serum creatinine levels. Kidney NGAL is also reportedly increased by kidney tubules very early after ischemic or nephrotoxic injury in both animal and human models and is rapidly secreted into the urine, sometimes preceding the appearance of other known urinary or serum markers of ischemic injury. Similarly, urinary IL-18 and KIM-1 are also detected at the onset of AKI. IL-18 is a proinflammatory cytokine and a mediator of ischemia-induced AKI in animal models. KIM-1 is a transmembrane glycoprotein that is not expressed in normal kidneys but is upregulated in proximal tubular cells after ischemic or nephrotoxic injury. With the growing number of biomarkers, the sensitivity of early detection, predisposition and diagnosis can be enhanced for renal disorders as well as increasing the time frame for administering prophylactic therapies to a subject.

ACTH

ACTH is a 39 amino acid peptide hormone secreted by the anterior pituitary gland. ACTH is secreted from the anterior pituitary in response to corticotropin-releasing hormone (CRH) that is secreted from the hypothalamus. The release of ACTH stimulates the adrenal cortex with subsequent increased production of glucocorticosteroids and/or cortisol from the adrenal cortex.

ACTH is synthesized from a precursor polypeptide pre-pro-opiomelanocortin (pre-POMC). The removal of the signal peptide during translation produces a 267 amino acid polypeptide POMC. POMC undergoes a series of post-translational modifications to yield various polypeptide fragments including and not limited to ACTH, β-lipotropin, γ-lipotropin, α, β, γ-Melanocyte Stimulating Hormone (MSH) and β-endorphin. POMC, ACTH and β-lipotropin are also secreted from the pituitary gland in response to the hormone corticotropin-releasing hormone (CRH). In some embodiments, the first 13 amino acids of $ACTH_{1-39}$ are cleaved to form α-melanocyte-stimulating hormone (α-MSH).

$ACTH_{1-39}$ is reported to act through the stimulation of cell surface ACTH receptors, which are located primarily on adrenocortical cells of the adrenal cortex. This results in the synthesis and secretion of glucocorticosteroids and/or mineral corticosteroids and/or androgenic steroids. Thus, in some embodiments, the methods of prophylactically treating renal disorders described herein (e.g., acute kidney injury or acute renal failure) which comprise administration of $ACTH_{1-39}$ or fragments thereof (e.g., $ACTH_{1-24}$, $ACTH_{1-17}$, $ACTH_{4-10}$, or analogs thereof) to an individual in need thereof, are associated, at least in part, with ACTH-mediated steroidogenesis.

The melanocortin receptor (type 2) (MCR2) is reported as a specific receptor for $ACTH_{1-39}$. However, Applicants have found that $ACTH_{1-39}$ is a pan-melanocortin receptor modulator. Accordingly, provided herein are methods for prophylactically treating renal disorders described herein (e.g., acute kidney injury or acute renal failure or renal damage due to ischemia) which comprise administration of ACTH to an individual in need thereof, and are associated, at least in part, with pan-melanocortin receptor modulation by ACTH.

In additional embodiments, the methods for prophylactically treating renal disorders described herein (e.g., acute kidney injury or acute renal failure or renal damage due to ischemia) which comprise administration of ACTH (e.g., $ACTH_{1-39}$ or fragments thereof (e.g., $ACTH_{1-24}$, $ACTH_{1-17}$, $ACTH_{4-10}$, or analogs thereof) to an individual in need thereof, are associated, at least in part, with both pan-melanocortin receptor modulation by ACTH, and ACTH mediated steroidogenesis.

In some instances, ACTH regulates response to acute kidney injury by pan-receptor binding to multiple melanocortin receptors. In some instances, ACTH suppresses renal inflammation associated with acute kidney injury by pan-receptor binding to multiple melanocortin receptors.

In some instances, multiple hypothalamic, pituitary, and peripheral factors regulate stress-mediated or inflammation-induced POMC expression and/or ACTH secretion. Essential cellular functions maintaining metabolic and neuroendocrine control require a homeostatic, non-stressed pattern of ACTH and glucocorticoid secretion. ACTH secretion is characterized by both circadian periodicity and ultradian pulsatility that is generated by CRH release and is also influenced by peripheral corticosteroids. Thus, ACTH secretion peaks at about before 7 am and nadir adrenal steroid secretion occurs between about 11 pm and 3 am, with periodic secretory bursts occurring throughout the day. Serum cortisol levels also exhibit a similar pattern of circadian periodicity. These rhythms are further reinforced by visual cues and the light-dark cycle. In some instances, stress results in increased ACTH pulse amplitude. In some instances, renal disorders (e.g., AKI) are associated with abnormality in the circadian periodicity and ultradian pulsatility of ACTH and/or cortisol levels in the body.

In some instances, an abnormality in ACTH levels is associated with inflammation (e.g., increased release of pro-inflammatory cytokines). In some instances, an abnormality in ACTH levels is associated with reduced VEGF secretion. In some instances, reduced VEGF secretion is associated with reduced growth of new blood vessels and inadequate oxygen supply to tissues (e.g., renal tissues).

In some instances, ACTH suppresses inflammation associated with renal disorders (e.g., AKI) by binding to melanocortin receptors.

Definitions

The term "ACTH", in some embodiments, includes corticotropin, adrenocorticotropic hormone, Tetracosactide or the like. In some embodiments, the term ACTH includes a 39 amino acid peptide hormone secreted by the anterior pituitary gland. In other embodiments the term "ACTH" also includes any ACTH peptide, any ACTH fragment, or any ACTH preparation as described herein. The term ACTH includes, in some embodiments, ACTH from any source including human ACTH, mouse ACTH, rat ACTH, porcine ACTH, sheep ACTH, bovine ACTH, rabbit ACTH or any other source of ACTH.

As used herein, in some embodiments, "ACTH peptide" refers to $ACTH_{1-39}$ peptide. In some embodiments, $ACTH_{1-39}$ peptide has the following structure (SEQ ID NO. 1):

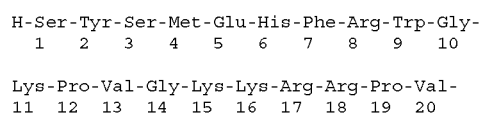

-continued

```
Lys-Val-Try-Pro-Asp-Gly-Ala-Glu-Asp-Gln-
21  22  23  24  25  26  27  28  29  30

Leu-Ala-Glu-Ala-Phe-Pro-Leu-Glu-Phe-OH
31  32  33  34  35  36  37  38  39.
```

The term ACTH includes peptides or peptide fragments, complexes, salts or aggregates with about 40%, about 45%, about 50%, about 55%, about 60%, about 65%, about 70%, about 75%, about 80%, about 85%, about 90%, or about 95% homology with $ACTH_{1-39}$. The term ACTH peptide includes ACTH peptide from any source including human ACTH, mouse ACTH, rat ACTH, porcine ACTH, sheep ACTH, bovine ACTH, rabbit ACTH or any other source of ACTH.

In some embodiments, ACTH is an ACTH preparation. As used herein, "ACTH preparation" refers to a mixture containing ACTH peptide and/or other peptide fragments and/or other proteins and/or other substances that together form a composition that is suitable for any methods and/or dosing regimen described herein. In some of such embodiments, ACTH is obtained from a homogenized pituitary extract of an appropriate animal (e.g., pituitary extract of a pig). Any suitable method is used to obtain a homogenized pituitary extract. In some of such embodiments, a homogenized pituitary extract includes ACTH peptide and/or other peptide fragments and/or other proteins and/or other substances that are contemplated as being part of the ACTH preparation that is compatible with any method described herein.

The term ACTH includes humanized and/or recombinant forms of ACTH and synthetic forms of ACTH. The term ACTH includes fragments of $ACTH_{1-39}$. Examples of synthetic forms and/or fragments of ACTH include and are not limited to $ACTH_{1-24}$ peptide having the formula (SEQ ID NO. 2):

```
H-Ser-Tyr-Ser-Met-Glu-His-Phe-Arg-Trp-Gly-
  1   2   3   4   5   6   7   8   9  10

Lys-Pro-Val-Gly-Lys-Lys-Arg-Arg-Pro-Val-
 11  12  13  14  15  16  17  18  19  20

Lys-Val-Try-Pro
 21  22  23  24
``` or a fragment, complex, aggregate, or analog thereof, or any combination thereof, $ACTH_{1-17}$ peptide having the formula (SEQ ID NO. 3):

```
H-Ser-Tyr-Ser-Met-Glu-His-Phe-Arg-Trp-Gly-
  1   2   3   4   5   6   7   8   9  10

Lys-Pro-Val-Gly-Lys-Lys-Arg-
 11  12  13  14  15  16  17
``` or a fragment, complex, aggregate, or analog thereof, or any combination thereof, $ACTH_{4-10}$ peptide (ORG-066) of formula (SEQ ID NO. 4):

```
Met-Glu-His-Phe-Arg-Trp-Gly
 4   5   6   7   8   9  10
``` or a fragment, complex, aggregate, or analog thereof, or any combination thereof, or $ACTH_{4-9}$ peptide analog (ORG-2766) of formula (SEQ ID NO. 6):

```
Met-Glu-His-Phe-D-Lys-Phe-OH
``` or a fragment, complex, aggregate, or analog thereof, or any combination thereof.

The term ACTH includes a peptide of formula (SEQ ID NO. 6):

```
Ac-Ser-Tyr-Ser-Met-Glu-His-Phe-Arg-Trp-Gly-Lys-

Pro-Val
``` or a fragment, complex, aggregate, or analog thereof, or any combination thereof, or a peptide fragment of formula (SEQ ID NO. 6):

```
H-Ser-Tyr-Ser-Met-Glu-His-Phe-Arg-Trp-Gly-Lys-

Pro-Val
``` or a fragment, complex, aggregate, or analog thereof, or any combination thereof, or a peptide fragment of formula (SEQ ID NO. 7):

```
D-Ala-Gln-Tyr-Phe-Arg-Trp-Gly-NH_2.
``` or a fragment, complex, aggregate, or analog thereof, or any combination thereof.

The term "ACTH aggregate" refers to a physical grouping of peptides which may comprise ACTH peptide, or fragments, analogs or homologs thereof. Such an aggregate may comprise hydrogen-bonded molecules and/or molecules held by bridging interactions via, for example, a salt bridge, a metal ion, and the like.

The term "ACTH complex" refers to ACTH or fragments or analogs thereof that are optionally complexed with other proteins (e.g., Bovine Serum Albumin), or metal ions, or charged polymers (e.g., polylysine), or fragments, homologs or analogs of ACTH, or any other suitable complexes that retain the functional characteristics of ACTH or ACTH fragments or analogs thereof and/or allow for formulation of ACTH or ACTH fragments or analogs thereof into suitable dosage forms.

In some embodiments, ACTH is an ACTH preparation. As used herein, "ACTH preparation" refers to a mixture containing ACTH peptide and/or other peptide fragments and/or other proteins and/or other substances that together form a composition that is suitable for any methods and/or dosing regimen described herein. In some of such embodiments, ACTH is obtained from a homogenized pituitary extract of an appropriate animal (e.g., pituitary extract of a pig). Any suitable method is used to obtain a homogenized pituitary extract. In some of such embodiments, a homogenized pituitary extract includes ACTH peptide and/or other peptide fragments and/or other proteins and/or other substances that are contemplated as being part of the ACTH preparation that is compatible with any method described herein.

The term "ACTH analog" or "analog of ACTH" refers to any compounds in which one or more atoms, functional groups, or substructures or amino acids in ACTH or fragments of ACTH have been replaced with different atoms, groups, or substructures or amino acids while retaining the functional activity of ACTH or fragments of ACTH. In some embodiments, an ACTH analog is a peptide fragment of ACTH$_{1-39}$ peptide that retains biological activity of ACTH, or in other words, has ACTH-like activity. One example of an ACTH analog is ACTH$_{4-9}$ peptide analog (ORG-2766) of formula (SEQ ID NO. 5):

Met-Glu-His-Phe-D-Lys-Phe-OH or a fragment, complex, aggregate, or analog thereof, or any combination thereof.

An ACTH analog is a compound in which one or more amino acids in ACTH, or homolog or fragment thereof is conservatively modified or substituted with another amino acid such that the modification does not impact the ACTH-like activity. As to amino acid substitutions, individual substitutions, deletions or additions to a peptide sequence which alters, adds or deletes a single natural and non-natural amino acid or a small percentage of natural and non-natural amino acids in the encoded sequence is a "conservatively modified analog" where the alteration results in the deletion of an amino acid, addition of an amino acid, or substitution of a natural and non-natural amino acid with a chemically similar amino acid, while retaining the biological activity of the ACTH peptide or fragment thereof. Conservative substitution tables providing functionally similar natural amino acids are well known in the art. For example, the following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(See, e.g., Creighton, Proteins: Structures and Molecular Properties (W H Freeman & Co.; 2nd edition (December 1993). In some embodiments, an ACTH analog has between 1-5 additional amino acid residues attached to the start or end of ACTH$_{1-39}$ peptide.

The term "ACTH fragment" includes any portion of the ACTH peptide ACTH$_{1-39}$. Examples of synthetic forms and/or fragments of ACTH include and are not limited to ACTH$_{1-24}$ peptide having the formula (SEQ ID NO. 2):

```
H-Ser-Tyr-Ser-Met-Glu-His-Phe-Arg-Trp-Gly-
  1   2   3   4   5   6   7   8   9   10

Lys-Pro-Val-Gly-Lys-Lys-Arg-Arg-Pro-Val-
 11  12  13  14  15  16  17  18  19  20

Lys-Val-Try-Pro
 21  22  23  24
``` or a fragment, complex, aggregate, or analog thereof, or any combination thereof, ACTH$_{1-17}$ peptide having the formula (SEQ ID NO. 3):

```
H-Ser-Tyr-Ser-Met-Glu-His-Phe-Arg-Trp-Gly-
  1   2   3   4   5   6   7   8   9   10

Lys-Pro-Val-Gly-Lys-Lys-Arg-
 11  12  13  14  15  16  17
``` or a fragment, complex, aggregate, or analog thereof, or any combination thereof, or ACTH$_{4-10}$ peptide (ORG-066) of formula (SEQ ID NO. 4):

```
Met-Glu-His-Phe-Arg-Trp-Gly
 4   5   6   7   8   9   10
``` or a fragment, complex, aggregate, or analog thereof, or any combination thereof.

The term ACTH fragment also includes alpha-MSH (ACTH$_{1-13}$) and d-alpha-MSH (SEQ ID NO. 6):

```
H-Ser-Tyr-Ser-Met-Glu-His-Phe-Arg-Trp-Gly-
  1   2   3   4   5   6   7   8   9   10

Lys-Pro-Val
 11  12  13 .
```

Any ACTH peptide, fragment, complex, aggregate, or analog or homolog thereof described above or below retains ACTH-like activity. As used herein, "ACTH-like activity", in some embodiments, may refer to activity of ACTH$_{1-39}$ peptide which is responsible for (1) steroidogenesis via interaction at, for example, melanocortin receptor MCR2, and/or (2) anti-inflammatory activity mediated via interaction of ACTH, or fragment, analog or homolog thereof at, for example, melanocotin receptors 1 and 3 (MCR1 and MCR3). Thus ACTH-like activity for a fragment arises from different domains of the ACTH$_{1-39}$ peptide. Accordingly, in one embodiment, ACTH-like activity at, for example, MCR2, resides in residues 14-39 of the ACTH$_{1-39}$ peptide. In a different embodiment, ACTH-like activity at, for example, MCR1 and MCR3, resides in residues 6-9 of the ACTH$_{1-39}$ peptide.

The term ACTH also includes synthetic preparations of ACTH that are commercially available including and not limited to ACTHAR® (corticotrophin) powder for injection or gel, SYNACTHEN® (tetracosactide), ADRENOMONE® (corticotrophin), or the like. Examples of commercially available ACTH peptides that are compatible with the methods described herein include and are not limited to Adrenocorticotropic Hormone (ACTH) (1-10) (human), Adrenocorticotropic Hormone (ACTH) (1-13) (human), Adrenocorticotropic Hormone (ACTH) (1-16) (human), Adrenocorticotropic Hormone (ACTH) (1-17) (human), Adrenocorticotropic Hormone (ACTH) (1-24) (human), Adrenocorticotropic Hormone (ACTH) (1-39) (human), Adrenocorticotropic Hormone (ACTH) (1-39) (rat), Adrenocorticotropic Hormone (ACTH) (18-39) (human), Adrenocorticotropic Hormone (ACTH) (4-10) (human), Adrenocorticotropic Hormone (ACTH) (1-4), Adrenocorticotropic Hormone (ACTH) (1-14) or the like available from, for example, GENSCRIPT®.

As used herein, the term ACTH also includes pre-POMC, POMC, β-lipotropin, γ-lipotropin, Melanocyte Stimulating Hormone (α-MSH, β-MSH, γ-MSH), β-endorphin, or the like, or any other polypeptide fragment that is a post-translational product of the POMC gene. POMC genes for various species are found in the NCBI GenBank including and not limited to human POMC transcript variant 1, mRNA, (NCBI Accession number NM_001035256), human POMC transcript variant 2, mRNA, (NCBI Accession number NM_000939), swine pro-opiomelanocortin, mRNA (NCI Accession number S73519), swine proopiomelanocortin protein (POMC) gene (NCBI Accession number EU184858), rat proopiomelanocortin (POMC) gene (NCBI Accession number K01877), or the like. Other examples of POMC genes include, for example, catfish POMC gene described in *Animal Genetics,* 2005, 36, 160-190.

The term "prodrug" refers to a precursor molecule that is a derivative of ACTH or ACTH fragments or analogs thereof that is suitable for incorporation in any dosage form described herein. A "prodrug" refers to a precursor compound that is converted into active compound in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, prodrugs facilitate transmittal across a cell membrane where water solubility is detrimental to mobility but which then is metabolically hydrolyzed to the carboxylic acid, the active entity, once inside the cell where water-solubility is beneficial. As non-limiting examples, a prodrug of ACTH or fragment of analog thereof is metabolically stable and is not degraded in the stomach.

Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or less labile and/or confers solubility or some other property to the drug. Once the chemical group has been cleaved and/or modified from the prodrug the active drug is generated. In some embodiments, a prodrug of ACTH or fragment or analog thereof is an alkyl ester of the parent compound such as, for example, methyl ester, ethyl ester, n-propyl ester, iso-propyl ester, n-butyl ester, sec-butyl ester, tert-butyl ester or any other ester.

Methods

Provided herein are methods of prophylactically treating individuals suspected of having, predisposed to, or at risk of developing a renal disorder comprising administration of ACTH to individuals in need thereof. In some embodiments, the methods of prophylactic treatment described herein allow for early intervention prior to onset of a renal disorder. In some embodiments, the methods of prophylactic treatment described herein are administered to individuals undergoing surgery. In other embodiments, the methods of prophylactic treatment described herein are administered to individuals who have sepsis. In yet other embodiments, upon detection of a biomarker described herein, the methods of treatment described herein allow for prophylactic administration of ACTH in individuals who are pre-disposed to a renal disorder. In certain instances, a renal disorder is chronic kidney disease. In other instances, a renal disorder is acute kidney injury.

In some embodiments, provided herein are methods of delaying onset or progression of a renal disorder comprising administration of adrenocorticotropic hormone (ACTH) peptide or fragment, analog, complex or aggregate thereof, or any combination thereof, to an individual suspected of having, predisposed to, or at risk of developing a renal disorder, wherein the ACTH peptide or fragment, analog, complex or aggregate thereof, or any combination thereof, is administered as a first dose and one or more subsequent doses. In some embodiments, administration of a dosing regimen of adrenocorticotropic hormone (ACTH) peptide or fragment, analog, complex or aggregate thereof, or any combination thereof, as described herein, to an individual suspected of having, predisposed to, or at risk of developing a renal disorder reduces or inhibits biomarkers described herein, thereby delaying onset or progression of a renal disorder. In certain instances, a renal disorder is chronic kidney disease. In other instances, a renal disorder is acute kidney injury.

In some embodiments, provided herein are methods of improving an impaired kidney function associated with a renal disorder comprising administration of adrenocorticotropic hormone (ACTH) peptide or fragment, analog, complex or aggregate thereof, or any combination thereof, to an individual suspected of having, predisposed to, or at risk of developing a renal disorder, wherein the ACTH peptide or fragment, analog, complex or aggregate thereof, or any combination thereof, is administered as a first dose and one or more subsequent doses. In certain instances, a renal disorder is chronic kidney disease. In other instances, a renal disorder is acute kidney injury.

In some embodiments, provided herein are methods of protecting against kidney impairment in an individual suspected of having, predisposed to, or at risk of developing a renal disorder comprising administration of adrenocorticotropic hormone (ACTH) peptide or fragment, analog, complex or aggregate thereof, or any combination thereof, wherein the ACTH peptide or fragment, analog, complex or aggregate thereof, or any combination thereof, is administered as a first dose and one or more subsequent doses. In certain instances, a renal disorder is chronic kidney disease. In other instances, a renal disorder is acute kidney injury.

In some embodiments, provided herein are methods of suppressing the release of pro-inflammatory cytokines associated with a renal disorder comprising administration of adrenocorticotropic hormone (ACTH) peptide or fragment, analog, complex or aggregate thereof, or any combination thereof, to an individual suspected of having, predisposed to, or at risk of developing a renal disorder, wherein the ACTH peptide or fragment, analog, complex or aggregate thereof, or any combination thereof, is administered as a first dose and one or more subsequent doses. In certain instances, a renal disorder is chronic kidney disease. In other instances, a renal disorder is acute kidney injury.

In some embodiments, provided herein are methods of increasing the depressed glomerular filtration rate (GFR) in an individual suspected of having, predisposed to, or at risk of developing a renal disorder comprising administration of adrenocorticotropic hormone (ACTH) peptide or fragment, analog, complex or aggregate thereof wherein the ACTH peptide or fragment, analog, complex or aggregate thereof, or any combination thereof, is administered as a first dose and one or more subsequent doses. In certain instances, a renal disorder is chronic kidney disease. In other instances, a renal disorder is acute kidney injury.

In some embodiments, provided herein are methods of decreasing elevated serum creatinine in an individual suspected of having, predisposed to, or at risk of developing a renal disorder comprising administration of adrenocorticotropic hormone (ACTH) peptide or fragment, analog, complex or aggregate thereof wherein the ACTH peptide or fragment, analog, complex or aggregate thereof, or any combination thereof, is administered as a first dose and one or more subsequent doses. In certain instances, a renal disorder is chronic kidney disease. In other instances, a renal disorder is acute kidney injury.

In some embodiments, provided herein are methods of decreasing elevated urinary protein levels in an individual suspected of having, predisposed to, or at risk of developing a renal disorder comprising administration of adrenocorticotropic hormone (ACTH) peptide or fragment, analog, complex or aggregate thereof wherein the ACTH peptide or fragment, analog, complex or aggregate thereof, or any combination thereof, is administered as a first dose and one or more subsequent doses. In certain instances, a renal disorder is chronic kidney disease. In other instances, a renal disorder is acute kidney injury.

In some embodiments, provided herein are methods of decreasing elevated asymmetric dimethylarginine (ADMA) in an individual suspected of having, predisposed to, or at risk of developing a renal disorder comprising administration of adrenocorticotropic hormone (ACTH) peptide or fragment, analog, complex or aggregate thereof wherein the ACTH peptide or fragment, analog, complex or aggregate thereof, or any combination thereof, is administered as a first dose and one or more subsequent doses. In certain instances, a renal disorder is chronic kidney disease. In other instances, a renal disorder is acute kidney injury.

In some embodiments, provided herein are methods of decreasing elevated liver-type fatty acid-binding protein (L-FABP) in an individual suspected of having, predisposed to, or at risk of developing a renal disorder comprising administration of adrenocorticotropic hormone (ACTH) peptide or fragment, analog, complex or aggregate thereof wherein the ACTH peptide or fragment, analog, complex or aggregate thereof, or any combination thereof, is administered as a first dose and one or more subsequent doses. In certain instances, a renal disorder is chronic kidney disease. In other instances, a renal disorder is acute kidney injury.

In some embodiments, provided herein are methods of decreasing elevated cystatin C (CysC) in an individual suspected of having, predisposed to, or at risk of developing a renal disorder comprising administration of adrenocorticotropic hormone (ACTH) peptide or fragment, analog, complex or aggregate thereof wherein the ACTH peptide or fragment, analog, complex or aggregate thereof, or any combination thereof, is administered as a first dose and one or more subsequent doses. In certain instances, a renal disorder is chronic kidney disease. In other instances, a renal disorder is acute kidney injury.

In some embodiments, provided herein are methods of decreasing elevated C-reactive Protein (CRP) in an individual suspected of having, predisposed to, or at risk of developing a renal disorder comprising administration of adrenocorticotropic hormone (ACTH) peptide or fragment, analog, complex or aggregate thereof wherein the ACTH peptide or fragment, analog, complex or aggregate thereof, or any combination thereof, is administered as a first dose and one or more subsequent doses. In certain instances, a renal disorder is chronic kidney disease. In other instances, a renal disorder is acute kidney injury.

In some embodiments, provided herein are methods of decreasing elevated soluble tumor necrosis factor receptor II (sTNFrii) in an individual suspected of having, predisposed to, or at risk of developing a renal disorder comprising administration of adrenocorticotropic hormone (ACTH) peptide or fragment, analog, complex or aggregate thereof wherein the ACTH peptide or fragment, analog, complex or aggregate thereof, or any combination thereof, is administered as a first dose and one or more subsequent doses. In certain instances, a renal disorder is chronic kidney disease. In other instances, a renal disorder is acute kidney injury.

In some embodiments, provided herein are methods of decreasing urinary neutrophil gelatinase-associated lipocalin (NGAL) in an individual suspected of having, predisposed to, or at risk of developing a renal disorder comprising administration of adrenocorticotropic hormone (ACTH) peptide or fragment, analog, complex or aggregate thereof wherein the ACTH peptide or fragment, analog, complex or aggregate thereof, or any combination thereof, is administered as a first dose and one or more subsequent doses. In certain instances, a renal disorder is chronic kidney disease. In other instances, a renal disorder is acute kidney injury.

In some embodiments, provided herein are methods of decreasing urinary interleukin-18 (IL-18) in an individual suspected of having, predisposed to, or at risk of developing a renal disorder comprising administration of adrenocorticotropic hormone (ACTH) peptide or fragment, analog, complex or aggregate thereof wherein the ACTH peptide or fragment, analog, complex or aggregate thereof, or any combination thereof, is administered as a first dose and one or more subsequent doses. In certain instances, a renal disorder is chronic kidney disease. In other instances, a renal disorder is acute kidney injury.

In some embodiments, provided herein are methods of decreasing urinary kidney injury molecule-1 (KIM-1) in an individual suspected of having, predisposed to, or at risk of developing a renal disorder comprising administration of adrenocorticotropic hormone (ACTH) peptide or fragment, analog, complex or aggregate thereof wherein the ACTH peptide or fragment, analog, complex or aggregate thereof, or any combination thereof, is administered as a first dose and one or more subsequent doses. In certain instances, a renal disorder is chronic kidney disease. In other instances, a renal disorder is acute kidney injury.

In some embodiments, administration of a dosing regimen of adrenocorticotropic hormone (ACTH) peptide or fragment, analog, complex or aggregate thereof, or any combination thereof, as described herein, to an individual suspected of having, predisposed to, or at risk of developing a renal disorder maintains pro-inflammatory cytokines associated with a renal disorder (e.g., maintain pro-inflammatory cytokine levels without any further changes) in the individual, or changes pro-inflammatory cytokine levels to partially normal or substantially normal levels. As used herein, a "change to substantially normal pro-inflammatory cytokine levels" refers to a change in physiological levels of pro-inflammatory cytokine levels in an individual suspected of having, predisposed to, or at risk of developing a renal disorder to levels that are substantially the same as the levels of pro-inflammatory cytokines in a normal individual. As used herein, substantially the same means, for example, about 90% to about 110% of the measured pro-inflammatory cytokine levels in a normal individual. In other embodiments, substantially the same means, for example, about 80% to about 120% of the measured pro-inflammatory cytokine levels in a normal individual when measured at the about same time. As used herein, "change to partially normal level of pro-inflammatory cytokines" refers to any change in pro-inflammatory cytokine levels in an individual suspected of having, predisposed to, or at risk of developing a renal disorder that trends towards pro-inflammatory cytokine levels of a normal individual when measured at about the same time. As used herein "partially normal pro-inflammatory cytokine level" is, for example, ±about 25%, ±about 35%, ±about 45%, ±about 55%, ±about 65%, or ±about 75% of the measured pro-inflammatory cytokine level of a normal individual when measured at the about same time.

In some embodiments, administration of a dosing regimen of adrenocorticotropic hormone (ACTH) peptide or fragment, analog, complex or aggregate thereof, or any combination thereof, as described herein, to an individual suspected of having, predisposed to, or at risk of developing a renal disorder maintains glomerular filtration rate disregulated with a renal disorder (e.g., maintain a glomerular filtration rate without any further changes) in the individual, or changes glomerular filtration rates to partially normal or substantially normal rates. As used herein, a "change to substantially normal glomerular filtration rate" refers to a change in physiological glomerular filtration rate in an individual suspected of having, predisposed to, or at risk of developing a renal disorder to levels that are substantially the same as the rates in a normal individual. As used herein, substantially the same means, for example, about 90% to about 110% of the glomerular filtration rate in a normal individual. In other embodiments, substantially the same means, for example, about 80% to about 120% of the glomerular filtration rate in a normal individual when measured at the about same time. As used herein, "change to partially normal glomerular filtration rate" refers to any change in glomerular filtration rate in an individual suspected of having, predisposed to, or at risk of developing a renal disorder that trends the glomerular filtration rate of a normal individual when measured at about the same time. As used herein "partially normal glomerular filtration rate" is, for example, ±about 25%, ±about 35%, ±about 45%, ±about 55%, ±about 65%, or ±about 75% of the measured glomerular filtration rate of a normal individual when measured at the about same time.

In some embodiments, administration of a dosing regimen of adrenocorticotropic hormone (ACTH) peptide or fragment, analog, complex or aggregate thereof, or any combination thereof, as described herein, to an individual suspected of having, predisposed to, or at risk of developing a renal disorder maintains serum creatinine levels associated and increased with a renal disorder (e.g., maintain serum creatinine levels without any further changes) in the individual, or changes serum creatinine levels to partially normal or substantially normal levels. As used herein, a "change to substantially normal serum creatinine levels" refers to a change in physiological levels of serum creatinine levels in an individual suspected of having, predisposed to, or at risk of developing a renal disorder to levels that are substantially the same as the levels of serum creatinine in a normal individual. As used herein, substantially the same means, for example, about 90% to about 110% of the measured serum creatinine levels in a normal individual. In other embodiments, substantially the same means, for example, about 80% to about 120% of the measured serum creatinine levels in a normal individual when measured at the about same time. As used herein, "change to partially normal level of serum creatinine" refers to any change in serum creatinine levels in an individual suspected of having, predisposed to, or at risk of developing a renal disorder that trends towards serum creatinine levels of a normal individual when measured at about the same time. As used herein "partially normal serum creatinine level" is, for example, ±about 25%, ±about 35%, ±about 45%, ±about 55%, ±about 65%, or ±about 75% of the measured serum creatinine level of a normal individual when measured at the about same time.

In some embodiments, administration of a dosing regimen of adrenocorticotropic hormone (ACTH) peptide or fragment, analog, complex or aggregate thereof, or any combination thereof, as described herein, to an individual suspected of having, predisposed to, or at risk of developing a renal disorder maintains urinary protein levels associated and increased with a renal disorder (e.g., maintain urinary protein levels without any further changes) in the individual, or changes urinary protein levels to partially normal or substantially normal levels. As used herein, a "change to substantially normal urinary protein levels" refers to a change in physiological levels of urinary protein levels in an individual suspected of having, predisposed to, or at risk of developing a renal disorder to levels that are substantially the same as the levels of urinary protein in a normal individual. As used herein, substantially the same means, for example, about 90% to about 110% of the measured urinary protein levels in a normal individual. In other embodiments, substantially the same means, for example, about 80% to about 120% of the measured urinary protein levels in a normal individual when measured at the about same time. As used herein, "change to partially normal level of urinary protein" refers to any change in urinary protein levels in an individual suspected of having, predisposed to, or at risk of developing a renal disorder that trends towards urinary protein levels of a normal individual when measured at about the same time. As used herein "partially normal urinary protein level" is, for example, ±about 25%, ±about 35%, ±about 45%, ±about 55%, ±about 65%, or ±about 75% of the measured urinary protein level of a normal individual when measured at the about same time.

In some embodiments, administration of a dosing regimen of adrenocorticotropic hormone (ACTH) peptide or fragment, analog, complex or aggregate thereof, or any combination thereof, as described herein, to an individual suspected of having, predisposed to, or at risk of developing a renal disorder maintains ADMA levels associated and increased with a renal disorder (e.g., maintain ADMA levels without any further changes) in the individual, or changes ADMA levels to partially normal or substantially normal levels. As used herein, a "change to substantially normal ADMA levels" refers to a change in physiological levels of ADMA levels in an individual suspected of having, predisposed to, or at risk of developing a renal disorder to levels that are substantially the same as the levels of ADMA in a normal individual. As used herein, substantially the same means, for example, about 90% to about 110% of the measured ADMA levels in a normal individual. In other embodiments, substantially the same means, for example, about 80% to about 120% of the measured ADMA levels in a normal individual when measured at the about same time. As used herein, "change to partially normal level of ADMA" refers to any change in ADMA levels in an individual suspected of having, predisposed to, or at risk of developing a renal disorder that trends towards ADMA levels of a normal individual when measured at about the same time. As used herein "partially normal ADMA level" is, for example, ±about 25%, ±about 35%, ±about 45%, ±about 55%, ±about 65%, or ±about 75% of the measured ADMA level of a normal individual when measured at the about same time.

In some embodiments, administration of a dosing regimen of adrenocorticotropic hormone (ACTH) peptide or fragment, analog, complex or aggregate thereof, or any combination thereof, as described herein, to an individual suspected of having, predisposed to, or at risk of developing a renal disorder maintains L-FABP levels associated and increased with a renal disorder (e.g., maintain L-FABP levels without any further changes) in the individual, or changes L-FABP levels to partially normal or substantially normal levels. As used herein, a "change to substantially normal L-FABP levels" refers to a change in physiological levels of L-FABP levels in an individual suspected of having, predisposed to, or at risk of developing a renal disorder to levels that are substantially the same as the levels of L-FABP in a normal individual. As used herein, substantially the same means, for example, about 90% to about 110% of the measured L-FABP levels in a normal individual. In other embodiments, substantially the same means, for example, about 80% to about 120% of the measured L-FABP levels in a normal individual when measured at the about same time. As used herein, "change to partially normal level of L-FABP" refers to any change in L-FABP levels in an individual suspected of having, predisposed to, or at risk of developing a renal disorder that trends towards L-FABP levels of a normal individual when measured at about the same time. As used herein "partially normal L-FABP level" is, for example, ±about 25%, ±about 35%, ±about 45%, ±about 55%, ±about 65%, or ±about 75% of the measured L-FABP level of a normal individual when measured at the about same time.

In some embodiments, administration of a dosing regimen of adrenocorticotropic hormone (ACTH) peptide or fragment, analog, complex or aggregate thereof, or any combination thereof, as described herein, to an individual suspected of having, predisposed to, or at risk of developing a renal disorder maintains CysC levels associated and increased with a renal disorder (e.g., maintain CysC levels without any further changes) in the individual, or changes CysC levels to partially normal or substantially normal levels. As used herein, a "change to substantially normal CysC levels" refers to a change in physiological levels of CysC levels in an individual suspected of having, predisposed to, or at risk of developing a renal disorder to levels that are substantially the same as the levels of CysC in a normal individual. As used herein, substantially the same means, for example, about 90% to about 110% of the measured CysC levels in a normal individual. In other embodiments, substantially the same means, for example, about 80% to about 120% of the measured CysC levels in a normal individual when measured at the about same time. As used herein, "change to partially normal level of CysC" refers to any change in CysC levels in an individual suspected of having, predisposed to, or at risk of developing a renal disorder that trends towards CysC levels of a normal individual when measured at about the same time. As used herein "partially normal CysC level" is, for example, ±about 25%, ±about 35%, ±about 45%, ±about 55%, ±about 65%, or ±about 75% of the measured CysC level of a normal individual when measured at the about same time.

In some embodiments, administration of a dosing regimen of adrenocorticotropic hormone (ACTH) peptide or fragment, analog, complex or aggregate thereof, or any combination thereof, as described herein, to an individual suspected of having, predisposed to, or at risk of developing a renal disorder maintains CRP levels associated and increased with a renal disorder (e.g., maintain CRP levels without any further changes) in the individual, or changes CRP levels to partially normal or substantially normal levels. As used herein, a "change to substantially normal CRP levels" refers to a change in physiological levels of CRP levels in an individual suspected of having, predisposed to, or at risk of developing a renal disorder to levels that are substantially the same as the levels of CRP in a normal individual. As used herein, substantially the same means, for example, about 90% to about 110% of the measured CRP levels in a normal individual. In other embodiments, substantially the same means, for example, about 80% to about 120% of the measured CRP levels in a normal individual when measured at the about same time. As used herein, "change to partially normal level of CRP" refers to any change in CRP levels in an individual suspected of having, predisposed to, or at risk of developing a renal disorder that trends towards CRP levels of a normal individual when measured at about the same time. As used herein "partially normal CRP level" is, for example, ±about 25%, ±about 35%, ±about 45%, ±about 55%, ±about 65%, or ±about 75% of the measured CRP level of a normal individual when measured at the about same time.

In some embodiments, administration of a dosing regimen of adrenocorticotropic hormone (ACTH) peptide or fragment, analog, complex or aggregate thereof, or any combination thereof, as described herein, to an individual suspected of having, predisposed to, or at risk of developing a renal disorder maintains sTNFrii levels associated and increased with a renal disorder (e.g., maintain sTNFrii levels without any further changes) in the individual, or changes sTNFrii levels to partially normal or substantially normal levels. As used herein, a "change to substantially normal sTNFrii levels" refers to a change in physiological levels of sTNFrii levels in an individual suspected of having, predisposed to, or at risk of developing a renal disorder to levels that are substantially the same as the levels of sTNFrii in a normal individual. As used herein, substantially the same means, for example, about 90% to about 110% of the measured sTNFrii levels in a normal individual. In other embodiments, substantially the same means, for example, about 80% to about 120% of the measured sTNFrii levels in a normal individual when measured at the about same time. As used herein, "change to partially normal level of sTNFrii" refers to any change in sTNFrii levels in an individual suspected of having, predisposed to, or at risk of developing a renal disorder that trends towards sTNFrii levels of a normal individual when measured at about the same time. As used herein "partially normal sTNFrii level" is, for example, ±about 25%, ±about 35%, ±about 45%, ±about 55%, ±about 65%, or ±about 75% of the measured sTNFrii level of a normal individual when measured at the about same time.

In some embodiments, administration of a dosing regimen of adrenocorticotropic hormone (ACTH) peptide or fragment, analog, complex or aggregate thereof, or any combination thereof, as described herein, to an individual suspected of having, predisposed to, or at risk of developing a renal disorder maintains NGAL levels associated and increased with a renal disorder (e.g., maintain NGAL levels without any further changes) in the individual, or changes NGAL levels to partially normal or substantially normal levels. As used herein, a "change to substantially normal NGAL levels" refers to a change in physiological levels of NGAL levels in an individual suspected of having, predisposed to, or at risk of developing a renal disorder to levels that are substantially the same as the levels of NGAL in a normal individual. As used herein, substantially the same means, for example, about 90% to about 110% of the measured NGAL levels in a normal individual. In other embodiments, substantially the same means, for example, about 80% to about 120% of the measured NGAL levels in a normal individual when measured at the about same time. As used herein, "change to partially normal level of NGAL" refers to any change in NGAL levels in an individual suspected of having, predisposed to, or at risk of developing a renal disorder that trends towards NGAL levels of a normal individual when measured at about the same time. As used herein "partially normal NGAL level" is, for example, ±about 25%, ±about 35%, ±about 45%, ±about 55%, ±about 65%, or ±about 75% of the measured NGAL level of a normal individual when measured at the about same time.

In some embodiments, administration of a dosing regimen of adrenocorticotropic hormone (ACTH) peptide or fragment, analog, complex or aggregate thereof, or any combination thereof, as described herein, to an individual suspected of having, predisposed to, or at risk of developing a renal disorder maintains IL-18 levels associated and increased with a renal disorder (e.g., maintain IL-18 levels without any further changes) in the individual, or changes IL-18 levels to partially normal or substantially normal levels. As used herein, a "change to substantially normal IL-18 levels" refers to a change in physiological levels of IL-18 levels in an individual suspected of having, predisposed to, or at risk of developing a renal disorder to levels that are substantially the same as the levels of IL-18 in a normal individual. As used herein, substantially the same means, for example, about 90% to about 110% of the measured IL-18 levels in a normal individual. In other embodiments, substantially the same means, for example, about 80% to about 120% of the measured IL-18 levels in a normal individual when measured at the about same time. As used herein, "change to partially normal level of IL-18" refers to any change in IL-18 levels in an individual suspected of having, predisposed to, or at risk of developing a renal disorder that trends towards IL-18 levels of a normal individual when measured at about the same time. As used herein "partially normal IL-18 level" is, for example, ±about 25%, ±about 35%, ±about 45%, ±about 55%, ±about 65%, or ±about 75% of the measured IL-18 level of a normal individual when measured at the about same time.

In some embodiments, administration of a dosing regimen of adrenocorticotropic hormone (ACTH) peptide or fragment, analog, complex or aggregate thereof, or any combination thereof, as described herein, to an individual suspected of having, predisposed to, or at risk of developing a renal disorder maintains KIM-1 levels associated and increased with a renal disorder (e.g., maintain KIM-1 levels without any further changes) in the individual, or changes KIM-1 levels to partially normal or substantially normal levels. As used herein, a "change to substantially normal KIM-1 levels" refers to a change in physiological levels of KIM-1 levels in an individual suspected of having, predisposed to, or at risk of developing a renal disorder to levels that are substantially the same as the levels of KIM-1 in a normal individual. As used herein, substantially the same means, for example, about 90% to about 110% of the measured KIM-1 levels in a normal individual. In other embodiments, substantially the same means, for example, about 80% to about 120% of the measured KIM-1 levels in a normal individual when measured at the about same time. As used herein, "change to partially normal level of KIM-1" refers to any change in KIM-1 levels in an individual suspected of having, predisposed to, or at risk of developing a renal disorder that trends towards KIM-1 levels of a normal individual when measured at about the same time. As used herein "partially normal KIM-1 level" is, for example, ±about 25%, ±about 35%, ±about 45%, ±about 55%, ±about 65%, or ±about 75% of the measured KIM-1 level of a normal individual when measured at the about same time.

In some embodiments, certain endpoints are used to determine therapeutic efficacy of administration of a dosing regimen of adrenocorticotropic hormone (ACTH) peptide or fragment, analog, complex or aggregate thereof, or any combination thereof, as described herein, to an individual suspected of having, predisposed to, or at risk of developing a renal disorder. Examples of such endpoints include changes in the biomarkers described herein, reduction in inflammation in kidney tissues, reduction in macrophages in kidney tissues, extension of survival, increased glomerular filtration rate, increased renal function, increased renal tubular cell function, reduction of symptoms associated with renal disorders (e.g., hypertension, fatigue, azotemia, uremia, hyperkalemia, anemia, edema, hyperphosphatemia and metabolic acidosis) or any other detectable and/or measurable endpoint.

Accordingly, in some embodiments of the methods described herein, following administration of ACTH to an suspected of having, predisposed to, or at risk of developing a renal disorder, the therapeutic efficacy of a dosing regimen of the ACTH preparation, ACTH peptide or fragment, analog, complex or aggregate thereof, or any combination thereof, as described herein, is evaluated by determination of changes in the biomarkers described herein. In some embodiments of the methods described herein, following administration of ACTH to an suspected of having, predisposed to, or at risk of developing a renal disorder, the therapeutic efficacy of a dosing regimen of the ACTH preparation, ACTH peptide or fragment, analog, complex or aggregate thereof, or any combination thereof, as described herein, is evaluated by determination of reduction in inflammation in kidney tissues. In some embodiments of the methods described herein, following administration of ACTH to an suspected of having, predisposed to, or at risk of developing a renal disorder, the therapeutic efficacy of a dosing regimen of the ACTH preparation, ACTH peptide or fragment, analog, complex or aggregate thereof, or any combination thereof, as described herein, is evaluated by determination of reduction in macrophages in kidney tissues. In some embodiments of the methods described herein, following administration of ACTH to an suspected of having, predisposed to, or at risk of developing a renal disorder, the therapeutic efficacy of a dosing regimen of the ACTH preparation, ACTH peptide or fragment, analog, complex or aggregate thereof, or any combination thereof, as described herein, is evaluated by determination of extension of survival. In some embodiments of the methods described herein, following administration of ACTH to an suspected of having, predisposed to, or at risk of developing a renal disorder, the therapeutic efficacy of a dosing regimen of the ACTH preparation, ACTH peptide or fragment, analog, complex or aggregate thereof, or any combination thereof, as described herein, is evaluated by determination of increased glomerular filtration rate. In some embodiments of the methods described herein, following administration of ACTH to an suspected of having, predisposed to, or at risk of developing a renal disorder, the therapeutic efficacy of a dosing regimen of the ACTH preparation, ACTH peptide or fragment, analog, complex or aggregate thereof, or any combination thereof, as described herein, is evaluated by determination of increased renal function. In some embodiments of the methods described herein, following administration of ACTH to an suspected of having, predisposed to, or at risk of developing a renal disorder, the therapeutic efficacy of a dosing regimen of the ACTH preparation, ACTH peptide or fragment, analog, complex or aggregate thereof, or any combination thereof, as described herein, is evaluated by determination of increased renal tubular cell function. In some embodiments of the methods described herein, following administration of ACTH to an suspected of having, predisposed to, or at risk of developing a renal disorder, the therapeutic efficacy of a dosing regimen of the ACTH preparation, ACTH peptide or fragment, analog, complex or aggregate thereof, or any combination thereof, as described herein, is evaluated by determination of reduction of symptoms associated with renal disorders (e.g., hypertension, fatigue, azotemia, uremia, hyperkalemia, anemia, edema, hyperphosphatemia and metabolic acidosis).

In certain specific embodiments of any of the methods described above, the adrenocorticotropic hormone (ACTH) peptide or fragment, analog, complex or aggregate thereof, or any combination thereof, suitable for the methods is $ACTH_{1-39}$. In certain specific embodiments of any of the methods described above, the adrenocorticotropic hormone (ACTH) peptide or fragment, analog, complex or aggregate thereof, or any combination thereof, suitable for the methods described herein is an ACTH preparation (e.g., ACTHAR® (corticotrophin)).

Dosing Regimen

In some embodiments of the methods of treatment of renal disorders (e.g., AKI) described above, the first dose and one or more subsequent doses of ACTH or fragment, analog, complex or aggregate thereof, or any combination thereof, are administered in a dosing regimen that is a pulsed dosing regimen (e.g., the dosing schedule produces escalating ACTH levels early in the dosing interval followed by a prolonged dose-free period). In some embodiments of the methods of treatment of renal disorders (e.g., AKI) described above, the first dose and one or more subsequent doses of ACTH or fragment, analog, complex or aggregate thereof, or any combination thereof, are administered in a dosing regimen that is not continuous (i.e., the intervals between doses are uneven). In some embodiments of the methods of treatment of renal disorders (e.g., AKI) described above, the first dose and one or more subsequent doses of ACTH or fragment, analog, complex or aggregate thereof, or any combination thereof, are administered in a dosing regimen that is a continuous dosing regimen.

In some embodiments, the first dose is administered upon detection of one or more symptoms of renal disorders (e.g., AKI). In some embodiments, the one or more subsequent doses are administered every day, every other day, every two days, every three days, every four days, every 5 days, every 6 days, once a week, every two weeks, every three weeks, once a month, every six weeks, every two months, every three months, every four months five months, every six months or any combination thereof.

In some embodiments, the dosing regimen comprises doses that produce decreasing levels of drug early in the dosing interval followed by a prolonged dose-free interval. In some embodiments, the dosing regimen comprises a first dose, a series of subsequent doses, followed by a drug holiday, and then, one or more series of doses that are the same as or different from the first series of doses. By way of example only, in one dosing regimen, the methods of treatment of renal disorders (e.g., AKI) describe above comprise administration of ACTH or fragment, analog, complex or aggregate thereof, or any combination thereof, and comprise a first dose of 80 IU, then a once daily dose of 20 IU for three days, followed by a 40 IU dose every week for a month, followed by a drug holiday for 3 months, and then a second series of doses comprising a first dose of 60 IU, then a once daily dose of 20 IU for three days, followed by a 40 IU dose every week for a month, followed by a drug holiday for 3 months.

In some embodiments, a dosing regimen comprises dosing that produces escalating levels of drug early in the dosing interval followed by a prolonged dose-free period. By way of example only, in one dosing regimen, the methods of treatment of renal disorders (e.g., AKI) describe above comprise administration of ACTH or fragment, analog, complex or aggregate thereof, or any combination thereof, and comprise a first dose of 20 IU, a second dose of 20 IU in the same week, then 40 IU twice a week, then 40 IU every other month for three months.

In some embodiments, a first dose of ACTH or fragment, analog, complex or aggregate thereof, or any combination thereof, is between about 10 IU, 20 IU, 30 IU, 40 IU, 50 IU, 60 IU, 70 IU, 80 IU to about 50 IU, 60 IU, 70 IU, 80 IU, 90 IU, 100 IU, 110 IU, 120 IU, 130 IU, 140 IU, 150 IU or 200 IU. In some embodiments, a first dose of ACTH or fragment, analog, complex or aggregate thereof, or any combination thereof, is between about 10 IU to about 200 IU, between about 10 IU to about 150 IU, between about 10 IU to about 100 IU, between about 10 IU to about 80 IU, between about 10 IU to about 60 IU, or between about 10 IU to about 40 IU. In some embodiments, a first dose of ACTH or fragment, analog, complex or aggregate thereof, or any combination thereof, is between about 10 IU to about 200 IU, between about 20 IU to about 200 IU, between about 40 IU to about 200 IU, between about 40 IU to about 150 IU, between about 40 IU to about 100 IU, between about 40 IU to about 80 IU, or between about 40 IU to about 60 IU. In some embodiments, a first dose of ACTH or fragment, analog, complex or aggregate thereof, or any combination thereof, is between about 20 IU to about 200 IU, between about 60 IU to about 150 IU, between about 60 IU to about 100 IU, or between about 60 IU to about 80 IU.

In some embodiments, a one or more subsequent dose of ACTH or fragment, analog, complex or aggregate thereof, or any combination thereof, is between about 10 IU, 20 IU, 30 IU, 40 IU, 50 IU, 60 IU, 70 IU, 80 IU to about 50 IU, 60 IU, 70 IU, 80 IU, 90 IU, 100 IU, 110 IU, 120 IU, 130 IU, 140 IU, 150 IU or 200 IU. In some embodiments, a one or more subsequent dose of ACTH or fragment, analog, complex or aggregate thereof, or any combination thereof, is between about 10 IU to about 200 IU, between about 10 IU to about 150 IU, between about 10 IU to about 100 IU, between about 10 IU to about 80 IU, between about 10 IU to about 60 IU, or between about 10 IU to about 40 IU. In some embodiments, a one or more subsequent dose of ACTH or fragment, analog, complex or aggregate thereof, or any combination thereof, is between about 20 IU to about 200 IU, between about 20 IU to about 150 IU, between about 20 IU to about 100 IU, between about 20 IU to about 80 IU, or between about 20 IU to about 60 IU, or between about 20 IU to about 40 IU. In some embodiments, a one or more subsequent dose of ACTH or fragment, analog, complex or aggregate thereof, or any combination thereof, is between about 40 IU to about 200 IU, between about 40 IU to about 150 IU, between about 40 IU to about 100 IU, between about 40 IU to about 80 IU, or between about 40 IU to about 60 IU. In some embodiments, a one or more subsequent dose of ACTH or fragment, analog, complex or aggregate thereof, or any combination thereof, is between about 20 IU to about 200 IU, between about 60 IU to about 150 IU, between about 60 IU to about 100 IU, or between about 60 IU to about 80 IU.

Where the ACTH, or fragment, analog, complex or aggregate thereof, or any combination thereof, is a synthetic preparation (i.e., not naturally occurring), in some embodiments, a first dose of ACTH or fragment, analog, complex or aggregate thereof, or any combination thereof, is between about 10 mg/kg, 20 mg/kg, 30 mg/kg, 40 mg/kg, 50 mg/kg, 60 mg/kg, 70 mg/kg, 80 mg/kg to about 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, 150 mg/kg or 200 mg/kg. In some embodiments, a first dose of ACTH or fragment, analog, complex or aggregate thereof, or any combination thereof, is between about 10 mg/kg to about 200 mg/kg, between about 20 mg/kg to about 200 mg/kg, between about 20 mg/kg to about 150 mg/kg, between about 20 mg/kg to about 100 mg/kg, between about 20 mg/kg to about mg/kg IU, between about mg/kg IU to about mg/kg IU, or between about 20 mg/kg to about 40 mg/kg. In some embodiments, a first dose of ACTH or fragment, analog, complex or aggregate thereof, or any combination thereof, is between about 40 mg/kg to about 200 mg/kg, between about 40 mg/kg to about 150 v, between about 40 mg/kg to about 100 mg/kg, between about 40 mg/kg to about 80 mg/kg, or between about 40 mg/kg to about 60 mg/kg. In some embodiments, a first dose of ACTH or fragment, analog, complex or aggregate thereof, or any combination thereof, is between about 20 mg/kg to about 200 mg/kg, between about 60 mg/kg to about 150 mg/kg, between about 60 mg/kg to about 100 mg/kg, or between about 60 mg/kg to about 80 mg/kg.

Where the ACTH, or fragment, analog, complex or aggregate thereof, or any combination thereof, is a synthetic preparation (i.e., not naturally occurring), in some embodiments, a one or more subsequent dose of ACTH or fragment, analog, complex or aggregate thereof, or any combination thereof, is between about 10 mg/kg, 20 mg/kg, 30 mg/kg, 40 mg/kg, 50 mg/kg, 60 mg/kg, 70 mg/kg, 80 mg/kg to about 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, 150 mg/kg or 200 mg/kg. In some embodiments, a one or more subsequent dose of ACTH or fragment, analog, complex or aggregate thereof, or any combination thereof, is between about 10 mg/kg to about 200 mg/kg, between about 10 mg/kg to about 150 mg/kg, between about 10 mg/kg to about 100 mg/kg, between about 10 mg/kg to about 80 mg/kg IU, between about 10 mg/kg IU to about 60 mg/kg IU, or between about 10 mg/kg to about 40 mg/kg. In some embodiments, a one or more subsequent dose of ACTH or fragment, analog, complex or aggregate thereof, or any combination thereof, is between about 20 mg/kg to about 200 mg/kg, between about 20 mg/kg to about 150 mg/kg, between about 20 mg/kg to about 100 mg/kg, between about 20 mg/kg to about 80 mg/kg, or between about 20 mg/kg to about 60 mg/kg. In some embodiments, a one or more subsequent dose of ACTH or fragment, analog, complex or aggregate thereof, or any combination thereof, is between about 40 mg/kg to about 200 mg/kg, between about 40 mg/kg to about 150 mg/kg, between about 40 mg/kg to about 100 mg/kg, between about 40 mg/kg to about 80 mg/kg, or between about 40 mg/kg to about 60 mg/kg. In some embodiments a one or more subsequent dose of ACTH or fragment, analog, complex or aggregate thereof, or any combination thereof, is between about 20 mg/kg to about 200 mg/kg, between about 60 mg/kg to about 150 mg/kg, between about 60 mg/kg to about 100 mg/kg, or between about 60 mg/kg to about 80 mg/kg.

In some embodiments, a one or more subsequent dose of ACTH or fragment, analog, complex or aggregate thereof, or any combination thereof, is between about 10%-90%, between about 20%-80%, between about 20%-60%, or between about 20%-40% of the first dose of ACTH or fragment, analog, complex or aggregate thereof, or any combination thereof. In some embodiments, a one or more subsequent dose of ACTH or fragment, analog, complex or aggregate thereof, or any combination thereof, is between about 80%-200%, between about 80%-175%, between about 80%-150%, between about 80%-125%, or between about 80%-100% of the first dose of ACTH or fragment, analog, complex or aggregate thereof, or any combination thereof.

In some embodiments, the ACTH peptide or fragment, analog, complex or aggregate thereof, or any combination thereof, is administered to an individual in need thereof in an amount sufficient to provide plasma cortisol secretion levels between about 0.1 to about 10 times, between about 0.5 to about 10 times, between about 1.1 to about 10 times, between about 1.1 to about 8 times, between about 1.1 to about 6 times, between about 1.1 to about 4 times, between about 1.1 to about 3 times, between about 1.1 to about 2 times, between about 1.1 to about 1.5 times the plasma cortisol secretion levels of a normal individual at about 8 am. In some embodiments, the ACTH peptide or fragment, analog, complex or aggregate thereof, or any combination thereof, is administered to an individual in need thereof in an amount sufficient to provide plasma cortisol secretion levels between about 0.1 to about 5 times, between about 0.5 to about 5 times, between about 1.5 to about 4 times, between about 1.5 to about 3 times, or between about 1.15 to about 2 times, the plasma cortisol secretion levels of a normal individual at about 8 am.

In some embodiments, the ACTH peptide or fragment, analog, complex or aggregate thereof, or any combination thereof, is administered to an individual in need thereof in an amount sufficient to provide plasma cortisol secretion levels between about 0.1 to about 10 times, between about 0.5 to about 10 times, between about 1.1 to about 10 times, between about 1.1 to about 8 times, between about 1.1 to about 6 times, between about 1.1 to about 4 times, between about 1.1 to about 3 times, between about 1.1 to about 2 times, or between about 1.1 to about 1.5 times the plasma cortisol secretion levels prior to administration of the ACTH peptide or fragment, analog, complex or aggregate thereof, or any combination thereof. In some embodiments, the ACTH peptide or fragment, analog, complex or aggregate thereof, or any combination thereof, is administered to an individual in need thereof in an amount sufficient to provide plasma cortisol secretion levels between about 0.1 to about 5 times, between about 0.5 to about 5 times, between about 1.5 to about 4 times, between about 1.5 to about 3 times, or between about 1.15 to about 2 times, the plasma cortisol secretion levels prior to administration of the ACTH peptide or fragment, analog, complex or aggregate thereof, or any combination thereof.

In some embodiments, the ACTH peptide or fragment, analog, complex or aggregate thereof, or any combination thereof, is administered in an amount sufficient to provide plasma cortisol concentration between about 1.5 to about 120 μg/100 mL over at least 24 hours after administration. In some embodiments, the ACTH peptide or fragment, analog, complex or aggregate thereof, or any combination thereof, is administered in an amount sufficient to provide plasma cortisol concentration between about 1.5 to about 60 μg/100 mL over at least 24 hours after administration. In some embodiments, the ACTH peptide or fragment, analog, complex or aggregate thereof, or any combination thereof, is administered in an amount sufficient to provide plasma cortisol concentration between about 1.5 to about 30 μg/100 mL over at least 24 hours after administration.

In some embodiments, where the patient's condition does not improve upon administration of a dosing regimen described herein, upon the doctor's discretion the ACTH peptide or fragment, analog, complex or aggregate thereof, or any combination thereof is optionally administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the ACTH peptide or fragment, analog, complex or aggregate thereof, or any combination thereof is optionally given continuously; alternatively, the dose of ACTH peptide or fragment, analog, complex or aggregate thereof, or any combination thereof being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the symptoms, to a level at which the improved disease, disorder or condition is retained. In some embodiments, patients require intermittent treatment on a long-term basis upon any recurrence of symptoms.

In some embodiments, the pharmaceutical compositions described herein are in unit dosage forms suitable for single administration of precise dosages. In unit dosage form, the formulation is divided into unit doses containing appropriate quantities of ACTH peptide or fragment, analog, complex or aggregate thereof, or any combination thereof. In some embodiments, the unit dosage is in the form of a package containing discrete quantities of the formulation. Non-limiting examples are packaged tablets or capsules, powders in vials or ampoules, or injectable suspension or solution in ampoules. In some embodiments, aqueous suspension compositions are packaged in single-dose non-reclosable containers. Alternatively, multiple-dose reclosable containers are used. In some of such embodiments, a preservative is optionally included in the composition. By way of example only, formulations for intramuscular injection are presented in unit dosage form, which include, but are not limited to ampoules, or in multi dose containers, with an added preservative.

Toxicity and therapeutic efficacy of such therapeutic regimens are optionally determined in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index, which is expressed as the ratio between LD50 and ED50. ACTH peptide or fragment, analog, complex or aggregate thereof, or any combination thereof, exhibiting high therapeutic indices are preferred. The data obtained from cell culture assays and animal studies (e.g., studies an animal model for renal disorders (e.g., AKI)) is optionally used in formulating a range of dosage for use in human. The dosage of such ACTH peptide or fragment, analog, complex or aggregate thereof, or any combination thereof lies preferably within a range of circulating concentrations that include the ED50 with minimal toxicity. The dosage optionally varies within this range depending upon the dosage form employed and the route of administration utilized.

Combination Therapy

In some embodiments of the methods and dosing regimens described above, an ACTH peptide or fragment, analog, complex or aggregate thereof, or any combination thereof, is administered in combination with other agents including, and not limited to, angiotensin-converting enzyme inhibitors (e.g., captopril, zofenopril, enalapril, ramipril, quinapril, perindopril, lisinopril, benazepril, fosinopril and related compounds), angiotensin receptor blockers (e.g., losartan, candesartan, valsartan, irbesartan, telmisartan, eprosartan, olmesartan and related compounds), phosphate binders (e.g., aluminium hydroxide, calcium carbonate, calcium acetate, lanthanum carbonate, sevelamer, calcium acetate/magnesium carbonate, and the like), hepatocyte growth factor (HGF), corticosteroids, erythropoietin, calcitriol, bardoxolone methyl, medoxomil, sulodexide, avosentan, combinations thereof, and the like.

In some embodiments of the methods and dosing regimens described above, an ACTH peptide or fragment, analog, complex or aggregate thereof, or any combination thereof, is administered in combination with agents that are used to treat symptoms of renal disorders including, but is not limited to, hypertension, fatigue, azotemia, uremia, hyperkalemia, anemia, edema, hyperphosphatemia and metabolic acidosis. Any known treatments and therapies for the symptoms of renal disorders can be used in combination with an ACTH peptide or fragment, analog, complex or aggregate thereof.

In other embodiments of the methods and dosing regimens described above, an ACTH peptide or fragment, analog, complex or aggregate thereof, or any combination thereof, is administered in combination with agents that are used to the underlying causes of renal disorders, including but not limited to diabetes, hypertension, glomerulonephritis, lupus, chronic infection, chronic inflammation, vascular disease, interstitial nephritis, congestive heart failure, sickle cell anemia and other blood dyscrasias, hepatitis, HIV, parvovirus and BK virus (a human polyomavirus), cystic kidney disease, congenital malformation, obstruction, malignancy, kidney disease of indeterminate cause, membranous glomerulonephritis, membranoproliferative glomerulonephritis, focal glomerular sclerosis, minimal change disease, cryoglobulinemia, Anti-Neutrophil Cytoplasmic Antibody (ANCA)-positive vasculitis, ANCA-negative vasculitis, amyloidosis, multiple myeloma, light chain deposition disease, complications of kidney transplant, chronic rejection of a kidney transplant, chronic allograft nephropathy, and the chronic effect of immunosuppressives. Any known treatments and therapies for the underlying causes of renal disorders can be used in combination with an ACTH peptide or fragment, analog, complex or aggregate thereof.

In some embodiments of combination therapy, the ACTH peptide or fragment, analog, complex or aggregate thereof, or any combination thereof, and the second therapeutic agent are administered simultaneously. In some embodiments of combination therapy, the ACTH peptide or fragment, analog, complex or aggregate thereof, or any combination thereof, and the second therapeutic agent are administered serially in any order. In some embodiments of combination therapy, the ACTH peptide or fragment, analog, complex or aggregate thereof, or any combination thereof, and the second therapeutic agent are administered at different intervals. By way of example only, a second therapeutic agent is administered after completion of a dosing regimen comprising administration of ACTH peptide or fragment, analog, complex or aggregate thereof, or any combination thereof.

Pharmaceutical Formulations

Provided herein, in certain embodiments, are compositions comprising at least one ACTH peptide or fragment, analog, complex or aggregate thereof, or any combination thereof, where the ACTH peptide or fragment, analog, complex or aggregate thereof, or any combination thereof, is as described herein.

Pharmaceutical compositions are formulated using one or more physiologically acceptable carriers including excipients and auxiliaries which facilitate processing of the ACTH peptide or fragment, analog, complex or aggregate thereof, or any combination thereof, into preparations which are used pharmaceutically. Proper formulation is dependent upon the route of administration chosen. A summary of pharmaceutical compositions is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

Provided herein are pharmaceutical compositions that include one or more of ACTH peptide or fragment, analog, complex or aggregate thereof, or any combination thereof, and a pharmaceutically acceptable diluent(s), excipient(s), or carrier(s). In addition, the ACTH peptide or fragment, analog, complex or aggregate thereof, or any combination thereof, is optionally administered as pharmaceutical compositions in which it is mixed with other active ingredients, as in combination therapy. In some embodiments, the pharmaceutical compositions includes other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions also contain other therapeutically valuable substances.

A pharmaceutical composition, as used herein, refers to a mixture of ACTH peptide or fragment, analog, complex or aggregate thereof, or any combination thereof, with other chemical components, such as carriers, stabilizers, diluents, dispersing agents, suspending agents, thickening agents, and/or excipients. In some embodiments, a pharmaceutical composition comprises an ACTH preparation (e.g., an ACTH peptide or fragment, analog, complex or aggregate thereof, or any combination thereof, and any other proteins and/or other substances that are present in a homogenized pituitary extract obtained from an appropriate animal source) and other chemical components, such as carriers, stabilizers, diluents, dispersing agents, suspending agents, thickening agents, and/or excipients. The pharmaceutical composition facilitates administration of ACTH peptide or fragment, analog, complex or aggregate thereof, or any combination thereof, to an organism. In practicing the methods of treatment or use provided herein, an ACTH peptide or fragment, analog, complex or aggregate thereof, or any combination thereof, are administered in a pharmaceutical composition to a mammal having a condition, disease, or disorder to be treated. Preferably, the mammal is a human. The does and dosing regimen varies depending on the severity and stage of the condition, the age and relative health of an individual, the potency of ACTH peptide or fragment, analog, complex or aggregate thereof, or any combination thereof, used and other factors. The ACTH peptide or fragment, analog, complex or aggregate thereof, or any combination thereof, is optionally used singly or in combination with one or more therapeutic agents as components of mixtures.

The pharmaceutical formulations described herein are optionally administered to a individual by multiple administration routes, including but not limited to, oral, parenteral (e.g., intravenous, subcutaneous, intramuscular, intrathecal), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

The pharmaceutical compositions will include at least one ACTH peptide or fragment, analog, complex or aggregate thereof, or any combination thereof, as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of ACTH peptide or fragment, analog, complex or aggregate thereof, or any combination thereof, having the same type of activity. In some situations, ACTH peptide or fragment, analog, complex or aggregate thereof, or any combination thereof, exist as tautomers and/or rotational isomers. All tautomers and/or rotational isomers are included within the scope of the embodiments presented herein. Additionally, ACTH peptide or fragment, analog, complex or aggregate thereof, or any combination thereof, exists in unsolvated as well as solvated forms with pharmaceutically acceptable solvents such as water, ethanol, and the like. The solvated forms of the ACTH peptide or fragment, analog, complex or aggregate thereof, or any combination thereof, presented herein are also considered to be disclosed herein. In some embodiments, ACTH peptide or fragment, analog, complex or aggregate thereof, or any combination thereof, exists as a complex with metal ions. The metal-ion complexed forms of the ACTH peptide or fragment, analog, complex or aggregate thereof, or any combination thereof, presented herein are also considered to be disclosed herein.

"Carrier materials" include any commonly used excipients in pharmaceutics and should be selected on the basis of compatibility with ACTH peptide or fragment, analog, complex or aggregate thereof, or any combination thereof, disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like.

Moreover, the pharmaceutical compositions described herein, which include a ACTH peptide or fragment, analog, complex or aggregate thereof, or any combination thereof, are formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In some embodiments, a formulation comprising a ACTH peptide or fragment, analog, complex or aggregate thereof, or any combination thereof, is a solid drug dispersion. A solid dispersion is a dispersion of one or more active ingredients in an inert carrier or matrix at solid state prepared by the melting (or fusion), solvent, or melting-solvent methods. (Chiou and Riegelman, Journal of Pharmaceutical Sciences, 60, 1281 (1971)). The dispersion of one or more active agents in a solid diluent is achieved without mechanical mixing. Solid dispersions are also called solid-state dispersions. In some embodiments, any ACTH peptide or fragment, analog, complex or aggregate thereof, or any combination thereof, described is formulated as a spray dried dispersion (SDD). An SDD is a single phase amorphous molecular dispersion of a drug in a polymer matrix. It is a solid solution prepared by dissolving the drug and a polymer in a solvent (e.g., acetone, methanol or the like) and spray drying the solution. The solvent rapidly evaporates from droplets which rapidly solidifies the polymer and drug mixture trapping the drug in amorphous form as an amorphous molecular dispersion. In some embodiments, such amorphous dispersions are filled in capsules and/or constituted into powders for reconstitution. Solubility of an SDD comprising a drug is higher than the solubility of a crystalline form of a drug or a non-SDD amorphous form of a drug. In some embodiments of the methods described herein, ACTH peptide or fragment, analog, complex or aggregate thereof, or any combination thereof, are administered as SDDs constituted into appropriate dosage forms described herein.

Pharmaceutical preparations for oral use are optionally obtained by mixing one or more solid excipient with a ACTH peptide or fragment, analog, complex or aggregate thereof, or any combination thereof, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross linked croscarmellose sodium, polyvinylpyrrolidone, agar, or alginic acid or a salt thereof such as sodium alginate. In some embodiments, a prodrug of the ACTH peptide or fragment, analog, complex or aggregate thereof, or any combination thereof, is used in preparations for oral use.

Dragee cores are provided with suitable coatings. For this purpose, concentrated sugar solutions are generally used, which optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments are optionally added to the tablets or dragee coatings for identification or to characterize different combinations of active compound doses.

In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bio-erodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations of a ACTH peptide or fragment, analog, complex or aggregate thereof, or any combination thereof, are optionally administered as a single capsule or in multiple capsule dosage form. In some embodiments, the pharmaceutical formulation is administered in two, or three, or four, capsules or tablets.

In another aspect, dosage forms include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Exemplary microencapsulation materials useful for delaying the release of the formulations including a ACTH peptide or fragment, analog, complex or aggregate thereof, or any combination thereof, include, but are not limited to, hydroxypropyl cellulose ethers (HPC) such as KLUCEL® (hydroxypropylcellulose) or Nisso HPC, low-substituted hydroxypropyl cellulose ethers (L-HPC), hydroxypropyl methyl cellulose ethers (HPMC) such as Seppifilm-LC, PHARMACOAT® (hypromellise) Metolose SR, METHOCEL®-E, (methylcellulose and hydroxypropyl methylcellulose polymer), Opadry YS, PrimaFlo, Benecel MP824, and Benecel MP843, methylcellulose polymers such as METHOCEL®-A, (methylcellulose and hydroxypropyl methylcellulose polymer), hydroxypropylmethylcellulose acetate stearate Aqoat (HF-LS, HF-LG, HF-MS) and METOLOSE® (methylcellulose/hydroxypropyl methylcellulose), Ethylcelluloses (EC) and mixtures thereof such as E461, ETHOCEL® (ethylcelluloses polymer), AQUALON®-EC, (ethylcelluloses ), SURELEASE® (aqueous ethylcellulose dispersion), Polyvinyl alcohol (PVA) such as Opadry AMB, hydroxyethylcelluloses such as NATROSOL® (hydroxyethylcellulose), carboxymethylcelluloses and salts of carboxymethylcelluloses (CMC) such as AQUALON®-CMC (sodium carboxymethylcellulose), polyvinyl alcohol and polyethylene glycol co-polymers such as KOLLICOAT IR® (polyvinyl alcohol and polyethylene glycol copolymer), monoglycerides (Myverol), triglycerides (KLX), polyethylene glycols, modified food starch, acrylic polymers and mixtures of acrylic polymers with cellulose ethers such as EUDRAGIT® EPO (Poly(butyl methacrylate-co-(2-dimethylaminoethyl) methacrylate-co-methyl methacrylate) 1:2:1), EUDRAGIT® L30D-55(Poly(methacrylic acid-co-ethyl acrylate) 1:1), EUDRAGIT® FS 30D (Poly(methyl acrylate-co-methyl methacrylate-co-methacrylic acid) 7:3:1) EUDRAGIT® L100-55(Poly(methacrylic acid-co-ethyl acrylate),1:1) EUDRAGIT® L100 (Poly(methacrylic acid-co-methyl methacrylate) 1:1) EUDRAGIT® S100 (Poly(methacrylic acid-co-methyl methacrylate) 1:2), EUDRAGIT® RD100[[Megan, I haven't been able to locate this one]], EUDRAGIT® E100 (Poly(butyl methacrylate-co-(2-demethylaminoethyl) methacrylate-co-methyl methacrylate) 1:2:1), EUDRAGIT® L12.5(Poly(methacrylic acid-co-methyl methacrylate) 1:1), EUDRAGIT® S12.5(Poly(methacrylic acid-co-methyl methacrylate) 1:2), EUDRAGIT® NE30D (Poly(ethyl acrylate-co-methyl methacrylate) 2:1),and EUDRAGIT® NE 40D (Poly(ethyl acrylate-co-methyl methacrylate) 2:1), cellulose acetate phthalate, sepifilms such as mixtures of HPMC and stearic acid, cyclodextrins, and mixtures of these materials.

The pharmaceutical solid oral dosage forms including formulations described herein, which include a ACTH peptide or fragment, analog, complex or aggregate thereof, or any combination thereof, are optionally further formulated to provide a controlled release of the ACTH peptide or fragment, analog, complex or aggregate thereof, or any combination thereof. Controlled release refers to the release of the ACTH peptide or fragment, analog, complex or aggregate thereof, or any combination thereof, from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a individual over an extended period of time according to a predetermined profile. Such release rates provide levels of ACTH peptide or fragment, analog, complex or aggregate thereof, or any combination thereof, for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In other embodiments, the formulations described herein, which include a ACTH peptide or fragment, analog, complex or aggregate thereof, or any combination thereof, are delivered using a pulsatile dosage form. A pulsatile dosage form is capable of providing one or more immediate release pulses at predetermined time points after a controlled lag time or at specific sites. Pulsatile dosage forms including the formulations described herein, which include a ACTH peptide or fragment, analog, complex or aggregate thereof, or any combination thereof, are optionally administered using a variety of pulsatile formulations that include, but are not limited to, those described in U.S. Pat. Nos. 5,011,692, 5,017,381, 5,229,135, and 5,840,329. Other pulsatile release dosage forms suitable for use with the present formulations include, but are not limited to, for example, U.S. Pat. Nos. 4,871,549, 5,260,068, 5,260,069, 5,508,040, 5,567,441 and 5,837,284.

Liquid formulation dosage forms for oral administration are optionally aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the ACTH peptide or fragment, analog, complex or aggregate thereof, or any combination thereof, the liquid dosage forms optionally include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions further includes a crystal-forming inhibitor.

In some embodiments, the pharmaceutical formulations described herein are self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase is optionally added just prior to administration, which ensures stability of an unstable or hydrophobic active ingredient. Thus, the SEDDS provides an effective delivery system for oral and parenteral delivery of hydrophobic active ingredients. In some embodiments, SEDDS provides improvements in the bioavailability of hydrophobic active ingredients. Methods of producing self-emulsifying dosage forms include, but are not limited to, for example, U.S. Pat. Nos. 5,858,401, 6,667,048, and 6,960,563.

Suitable intranasal formulations include those described in, for example, U.S. Pat. Nos. 4,476,116, 5,116,817 and 6,391,452. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents are optionally present.

For administration by inhalation, the ACTH peptide or fragment, analog, complex or aggregate thereof, or any combination thereof, is optionally in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit is determined by providing a valve to deliver a metered amount. Capsules and cartridges of, such as, by way of example only, gelatin for use in an inhaler or insufflator are formulated containing a powder mix of the ACTH peptide or fragment, analog, complex or aggregate thereof, or any combination thereof, and a suitable powder base such as lactose or starch.

Buccal formulations that include a ACTH peptide or fragment, analog, complex or aggregate thereof, or any combination thereof, include, but are not limited to, U.S. Pat. Nos. 4,229,447, 4,596,795, 4,755,386, and 5,739,136. In addition, the buccal dosage forms described herein optionally further include a bioerodible (hydrolysable) polymeric carrier that also serves to adhere the dosage form to the buccal mucosa. The buccal dosage form is fabricated so as to erode gradually over a predetermined time period, wherein the delivery of the ACTH peptide or fragment, analog, complex or aggregate thereof, or any combination thereof, is provided essentially throughout. Buccal drug delivery avoids the disadvantages encountered with oral drug administration, e.g., slow absorption, degradation of the active agent by fluids present in the gastrointestinal tract and/or first-pass inactivation in the liver. The bioerodible (hydrolysable) polymeric carrier generally comprises hydrophilic (water-soluble and water-swellable) polymers that adhere to the wet surface of the buccal mucosa. Examples of polymeric carriers useful herein include acrylic acid polymers and co, e.g., those known as "carbomers" (CARBOPOL® (carbomer), which may be obtained from B.F. Goodrich, is one such polymer). Other components also be incorporated into the buccal dosage forms described herein include, but are not limited to, disintegrants, diluents, binders, lubricants, flavoring, colorants, preservatives, and the like. For buccal or sublingual administration, the compositions optionally take the form of tablets, lozenges, or gels formulated in a conventional manner.

Transdermal formulations of a ACTH peptide or fragment, analog, complex or aggregate thereof, or any combination thereof, are administered for example by those described in U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

The transdermal formulations described herein include at least three components: (1) a formulation of a ACTH peptide or fragment, analog, complex or aggregate thereof, or any combination thereof; (2) a penetration enhancer; and (3) an aqueous adjuvant. In addition, transdermal formulations include components such as, but not limited to, gelling agents, creams and ointment bases, and the like. In some embodiments, the transdermal formulation further includes a woven or non-woven backing material to enhance absorption and prevent the removal of the transdermal formulation from the skin. In other embodiments, the transdermal formulations described herein maintain a saturated or supersaturated state to promote diffusion into the skin.

In some embodiments, formulations suitable for transdermal administration of a ACTH peptide or fragment, analog, complex or aggregate thereof, or any combination thereof, employ transdermal delivery devices and transdermal delivery patches and are lipophilic emulsions or buffered, aqueous solutions, dissolved and/or dispersed in a polymer or an adhesive. Such patches are optionally constructed for continuous, pulsatile, or on demand delivery of pharmaceutical agents. Still further, transdermal delivery of the ACTH peptide or fragment, analog, complex or aggregate thereof, or any combination thereof, is optionally accomplished by means of iontophoretic patches and the like. Additionally, transdermal patches provide controlled delivery of the ACTH peptide or fragment, analog, complex or aggregate thereof, or any combination thereof. The rate of absorption is optionally slowed by using rate-controlling membranes or by trapping the ACTH peptide or fragment, analog, complex or aggregate thereof, or any combination thereof, within a polymer matrix or gel. Conversely, absorption enhancers are used to increase absorption. An absorption enhancer or carrier includes absorbable pharmaceutically acceptable solvents to assist passage through the skin. For example, transdermal devices are in the form of a bandage comprising a backing member, a reservoir containing the ACTH peptide or fragment, analog, complex or aggregate thereof, or any combination thereof, optionally with carriers, optionally a rate controlling barrier to deliver the ACTH peptide or fragment, analog, complex or aggregate thereof, or any combination thereof, to the skin of the host at a controlled and predetermined rate over a prolonged period of time, and means to secure the device to the skin.

Formulations that include a ACTH peptide or fragment, analog, complex or aggregate thereof, or any combination thereof, suitable for intramuscular, intrathecal, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

For intravenous injections, a ACTH peptide or fragment, analog, complex or aggregate thereof, or any combination thereof, is optionally formulated in aqueous solutions, preferably in physiologically compatible buffers such as Hank's solution, Ringer's solution, or physiological saline buffer.

For transmucosal administration, penetrants appropriate to the barrier to be permeated are used in the formulation. For other parenteral injections including intrathecal and intramuscular injections, appropriate formulations include aqueous or nonaqueous solutions, preferably with physiologically compatible buffers or excipients.

Parenteral injections optionally involve bolus injection or continuous infusion. Formulations for injection are optionally presented in unit dosage form, e.g., in ampoules or in multi dose containers, with an added preservative. In some embodiments, the pharmaceutical composition described herein are in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of the ACTH peptide or fragment, analog, complex or aggregate thereof, or any combination thereof, in water soluble form. Additionally, suspensions of the ACTH peptide or fragment, analog, complex or aggregate thereof, or any combination thereof, are optionally prepared as appropriate oily injection suspensions.

In some embodiments, the ACTH peptide or fragment, analog, complex or aggregate thereof, or any combination thereof, is administered topically and formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

The ACTH peptide or fragment, analog, complex or aggregate thereof, or any combination thereof, is also optionally formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

EXAMPLES

Example 1

Pretreatment of ACTH in a TNF Induced Acute Kidney Injury (AKI) Animal Model

Rats were maintained on a 12 hr light: 12 hr dark cycle and supplied with rat chow and water ad lib. Animals were divided into groups that received various doses of ACTHAR® (corticotrophin) gel along with a group that received no treatment.

Acute Kidney Injury was induced in the animals via Tumor Necrosis Factor (TNF) injection. In these models, TNF raised blood pressure, reduced glomerular filtration rate, and resulted in 40% mortality within 8 hours. TNF induced a pattern of AKI, characterized by vacuolization of proximal tubular epithelium, epithelial necrosis, sloughing of brush border and tubular cells into lumen, nuclear enlargement and pleomorphism, and prominent inflammation.

At a low dose, pretreatment with ACTH normalized increased survival, improved kidney function, normalized systemic and renal hemodynamics. Morphologic evidence of injury was also remarkably attenuated by ACTH. In the ACTH treated animals, reductions in renal inflammation and apoptosis was observed. It was further observed that ACTH suppressed renal inflammation in a dose dependent manner, marked by diminished number of exogenously infused, fluorescence-labeled macrophages that were sequestered in the kidney. TNF induced renal cell apoptosis, assessed by caspase-3 cleavage and terminal deoxynucleotidyl transferase dUTP nick end labeling, was also markedly reduced by ACTH.

It is contemplated that the observed protective effect may be attributed to ACTH's action on the adrenal gland to raise serum levels of anti-inflammatory corticosterone. However, it was also observed that the steroidogenic response to ACTH above a dose of 5 IU/Kg reached a plateau, the renoprotective effect continued to increase with even higher doses, suggesting that steroid independent mechanisms also contribute to ACTH's protective effects.

Examples 1A-1E

Following the procedure described above, $ACTH_{1-39}$, $ACTH_{1-24}$, $ACTH_{1-17}$, $ACTH_{4-10}$, $ACTH_{4-9}$ analog, are also tested in an animal model of TNF induced AKI.

Example 2

Pretreatment of ACTH in Acute Kidney Injury (AKI) Animal Model

Male Sprague Dawley rats weighing 200-300 g are maintained on a 12 hr light: 12 hr dark cycle and supplied with rat chow and water ad lib. Acute Kidney Injury is induced via ischemic/reperfusion (I/R) in the animals as described in Tögel et al. 2005, *Am J Physiol Renal Physiol* 289:31-42). Briefly, a midabdominal laparatomy is performed in isoflurane-anesthetized animals, exposing the kidneys and renal pedicles which are clamped with atraumatic vascular clamps for 40 minutes.

Prior to induction of I/R AKI, the animals are divided into the 4 groups: (1) No ACTH treatment; (2) pretreatment with 10 IU/kg ACTHAR® gel every day for one week (3) pretreatment with 2 IU/kg ACTHAR® gel every day for one week; and (4) pretreatment with 10 IU/kg ACTHAR® gel every day for one month.

Protective effects of continuous dosing of ACTH are based on increased survival, improved kidney function, normalized systemic and renal hemodynamics, and reductions in renal inflammation and apoptosis. Injury morphology is also assessed in ACTH pretreated and untreated animals. Inflammation is measured by numbers of tissue staining of macrophages sequestered in the kidney. TNF induced renal cell apoptosis is assessed by measuring biomarkers including caspase-3 cleavage and terminal deoxynucleotidyl transferase dUTP nick end labeling.

Examples 2A-2E

Following the procedure described above, $ACTH_{1-39}$, $ACTH_{1-24}$, $ACTH_{1-17}$, $ACTH_{4-10}$, $ACTH_{4-9}$ analog, are also tested for pretreatment in an animal model of AKI.

Example 3

ACTH and Chronic Kidney Disease (CKD) Animal Model

Heterozygous $COL4A3^{+/-}$ mice are used as a model for CKD. Cross-breeding and PCR-based genotyping of heterozygous $COL4A3^{+/-}$, homozygous $COL4A3^{-/-}$, and wildtype control mice on SvJ/129 genetic background are performed as described previously in Bierowski et al. 2006, *J Am Soc Nephrology*, 17:1986-1994.

Heterozygous $COL4A3^{+/-}$ and wildtype SvJ/129 mice are divided into vehicle and treatment groups (4 groups total). ACTHAR® gel treatment is initiated 30 days after birth and continued until the end stage. Each animal is given a first dose followed by a subsequent weekly dose of ACTHAR® gel. All animals are maintained on a 12 hours light/dark cycle. Various tests are routinely performed starting from 7.5 weeks of age. A subset of the animal groups are killed after 30 wks and 12 mo. for light and electron microscopy and immunohistochemistry. The rest of the animals left alive until natural death to monitor lifespan.

Proteinuria and Urine Analyses:

Proteinuria is measured using a gradient polyacrylamide gel, stained with Coomassie Blue, and analyzed by densitometry, a semiquantitative method described before (Bierowski et al. 2006); each animal is sampled at several time points. Serum urea is determined on a Hitachi 917 Automatic analyzer (Boehringer Mannheim, Mannheim, Germany) that was validated on a daily basis; each animal is sampled at one time point. Hematuria is evaluated by phase contrast microscopy on a Zeiss light microscope. Hematuria is defined as more than five erythrocytes per visual field (magnification ×400). Serum urea and proteinuria are measured after 7.5, 9.5, 12, and 30 wk and 12, 18, 24, and 30 mo.

Microscopy:

Animals are killed by cardiac puncture and intracardially perfused with a solution that contains 10,000 i.e./L heparin (Liquaemin N 25000; Hoffmann-La Roche, Mannheim, Germany) and 1% procainhydrochloride in 0.1 M PBS and half-strength Karnovsky fixative (4% paraformaldehyde and 2% glutardialdehyde in 0.1 M sodium cacodylate [pH 7.3]). Kidney samples are immersion-fixed for 1 to 2 d and processed further for embedding in Araldite as described previously (Bierowski et al. 2006). Renal cortex from each mouse is cut and at least five glomeruli per mouse were examined with a Zeiss Axiophot light and Zeiss EM 902 electron microscope.

Immunohistochemistry:

For paraffin embedding, kidneys are fixed in 4% paraformaldehyde plus 0.1 mol/L PBS and vacuum embedded using a Shandon Citadel 1000 automatic embedding machine (Pittsburgh, Pa.). Sections of 4 to 5 μm thickness are cut on a Microm HM355S (Walldorf, Germany) microtome. Sections are rehydrated, treated with Trypsin for 7 min, and blocked with 5% BSA at room temperature. The primary antibody is incubated overnight at 4° C. (rabbit anti-mouse EHS-laminin and rabbit anti-mouse fibronectin, 1:1000; gift from M. Paulsson, Cologne, Germany). Goat anti-rabbit Cy3 (Jackson ImmunoResearch Laboratories, West Grove, Pa.) served as secondary antibody. PDX conjugated anti-smooth muscle actin (DAKO, Hamburg, Germany) and rat anti-mouse F4/80 with a goat anti-rat IgG horseradish peroxidase secondary antibody (Serotec, Oxford, England) are used to stain activated fibroblasts and macrophages on hemalaun-counterstained paraffin sections.

An improvement in lifespan and/or normalized renal morphology in the ACTH treated CKD mice with respect untreated CKD mice is indicative of a therapeutic effect of ACTHAR® gel.

Examples 3A-3E

Following the procedure described above, $ACTH_{1-39}$, $ACTH_{1-24}$, $ACTH_{1-17}$, $ACTH_{4-10}$, $ACTH_{4-9}$ analog, are also tested for pretreatment in an animal model of chronic kidney disease.

Example 4

Clinical Trial on ACTH for the Prevention of Contrast-Induced Acute Kidney Injury in Surgery Purpose: This trial evaluates whether treatment with ACTHAR® gel (ACTH) will reduce the incidence of AKI in subjects with CKD and additional risk factors. Adult subjects with moderate to severe CKD who are undergoing coronary angiography and percutaneous coronary intervention (PCI) are randomized to either placebo or a dosage regimen of ACTHAR® gel and followed for 90 days. Subjects receive 4 weeks of randomized therapy starting prior to angiography. The primary endpoint of the trial is the difference in mean paired change of a panel of sensitive renal biomarkers between the groups. Differences in renal or cardiovascular clinical events will also be evaluated.

Study Type: A Phase II, Randomized, Double-Blind, Placebo-Controlled Trial to Assess the Efficacy and Safety of ACTHAR® gel in Contrast-Induced Acute Oxidative Kidney Injury Study Design:

| Arms | Assigned Interventions |
|---|---|
| ACTHAR ® gel: Experimental Intervention: Drug: ACTHAR ® gel (ACTH) | Drug: ACTHAR ® gel Subjects will be administered 20 IU intramuscularly twice a week for two weeks and 40 IU for the following two weeks prior to angiography |
| Placebo: Placebo Comparator Intervention: Drug: Placebo | Drug: Placebo Subjects will be administered a placebo intramuscularly twice a week for two weeks and a placebo for the following two weeks prior to angiography |

Primary Outcome Measures: Biomarker evidence of Acute Kidney injury [Time Frame: 8 Days]
  Mean paired change in a panel of acute kidney injury (AKI) biomarkers (urinary NGAL, L-FABP, interleukin-18 (IL-18), kidney injury molecule-1 (KIM-1), urinary alpha GST (proximal tubular injury), Pi GST (distal tubular injury) and cystatin C; serum cystatin C) from baseline (Day 1) to peak in the ACTHAR® gel and placebo treatment groups, within 192 hours of contrast exposure
Secondary Outcome Measures: Incidence of Acute Kidney Injury [Time Frame: 48 hours]
  Incidence of AKI defined as an absolute increase in serum Cr of ≥0.3 mg/dL, and/or a 50% relative increase in serum Cr from baseline (Day 1) to a maximum value obtained within 48 hours of contrast exposure
Estimated Enrollment: 60
Eligibility:
Ages Eligible for Study: 18 years or older
Genders Eligible for Study: Both
Inclusion Criteria:
  estimated Glomerular Filtration Rate of <60 ml/min/1.73 m²
  Presence of at least one additional risk factor: (1) diabetes mellitus, (2) Age≥75 years, (3) left ventricular ejection fraction≤40%
Exclusion Criteria:
End-Stage Renal Disease
Recent change in serum creatinine
Primary PCI for ST-segment-elevation myocardial infarction
Currently receiving mechanical ventilation
Severe heart failure or cardiogenic shock
Requirement for inotropic support (prior 30 days)
Sustained hypertension≥200/100
Absolute neutrophil count<1500
Hemoglobin<8 gm/dL
Subject not expected to live for 90 days

Example 5

Pharmaceutical Compositions

Example 5a

Parenteral Composition

To prepare a parenteral pharmaceutical composition suitable for administration by intrathecal or intramuscular or intravenous or subcutaneous injection, 100 mg of a water-soluble salt of ACTH peptide or fragment, analog, complex or aggregate thereof, or any combination thereof, described herein, is dissolved in DMSO and then mixed with 10 mL of 0.9% sterile saline. A preservative and/or a stabilizer is optionally added to the mixture. The mixture is incorporated into a dosage unit form suitable for administration by injection.

Example 5b

Inhalation Composition

To prepare a pharmaceutical composition for inhalation delivery, 20 mg of ACTH peptide or fragment, analog, complex or aggregate thereof, or any combination thereof, is mixed with 50 mg of anhydrous citric acid and 100 mL of 0.9% sodium chloride solution. The mixture is incorporated into an inhalation delivery unit, such as a nebulizer, which is suitable for inhalation administration.

Example 5c

Rectal Gel Composition

To prepare a pharmaceutical composition for rectal delivery, 100 mg of ACTH peptide or fragment, analog, complex or aggregate thereof, or any combination thereof, is mixed with 2.5 g of methylcellulose (1500 mPa), 100 mg of methylparapen, 5 g of glycerin and 100 mL of purified water. The resulting gel mixture is then incorporated into rectal delivery units, such as syringes, which are suitable for rectal administration.

Example 5d

Topical Gel Composition

To prepare a pharmaceutical topical gel composition, 100 mg of ACTH peptide or fragment, analog, complex or aggregate thereof, or any combination thereof, is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Example 5e

Oral Composition

To prepare a pharmaceutical composition for oral delivery, 100 mg of ACTH peptide or fragment, analog, complex or aggregate thereof, or any combination thereof, or a prodrug thereof, is mixed with 750 mg of starch. The mixture is incorporated into an oral dosage unit, such as a hard gelatin capsule, which is suitable for oral administration.

Example 5f

Nasal Spray Solution

To prepare a pharmaceutical nasal spray solution, 10 g of ACTH peptide or fragment, analog, complex or aggregate thereof, or any combination thereof, is mixed with 30 mL of a 0.05M phosphate buffer solution (pH 4.4). The solution is placed in a nasal administrator designed to deliver 100 µl of spray for each application.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of prophylactically treating acute kidney injury (AKI) in an individual in need thereof, comprising selecting an individual suspected of having, predisposed to, or at risk of developing acute kidney injury, and administering an adrenocorticotropic hormone (ACTH) peptide to the individual in need thereof, wherein the ACTH peptide is administered as a first dose and one or more subsequent doses; and wherein the ACTH peptide is an ACTH peptide preparation comprising ACTH peptides having about 90% or greater homology with full length porcine ACTH.

2. The method of claim 1, wherein the ACTH peptide in the preparation is derived from porcine pituitary glands.

3. The method of claim 1, wherein the ACTH peptide preparation is formulated in a gel.

4. The method of claim 1, wherein the individual is undergoing surgery.

5. The method of claim 1, wherein the individual has sepsis.

6. The method of claim 1, wherein the selection of the individual is based upon a change in a kidney biomarker in the individual as compared to a normal baseline level of the kidney biomarker in the general population.

7. The method of claim 1, wherein the selection of an individual is based upon a decrease in a glomerular filtration rate (GFR) level as compared to a normal baseline level, an increase in a serum creatinine level as compared to a normal baseline level, an increase in a urinary protein level as compared to a normal baseline level, an elevated asymmetric dimethylarginine (ADMA) level as compared to a normal baseline level, an elevated cystatin C (CysC) level as compared to a normal baseline level, an elevated C-reactive Protein (CRP) level as compared to a normal baseline level, or an elevated soluble tumor necrosis factor receptor II (sTNFrii) level as compared to a normal baseline level.

8. The method of claim 1, wherein the selection of an individual is based upon detection of urinary neutrophil gelatinase-associated lipocalin (NGAL), detection of urinary interleukin-18 (IL-18), urinary kidney injury molecule-1 (KIM-1), or decreased urine output.

9. The method of claim 1, wherein the first dose of the ACTH peptide preparation comprises a dose between about 10 IU and about 150 IU, and the one or more subsequent doses of the ACTH peptide preparation is administered about every day, about every 2 days, about every 5 days, about every week, about every two weeks, about every three weeks, about every month, about every two months, or any combination thereof.

10. The method of claim 1, wherein the first dose of the ACTH peptide preparation comprises a dose between about 10 IU and about 150 IU, and the one or more subsequent doses of the ACTH peptide preparation are between about 20%-80% of the first dose.

11. The method of claim 1, wherein the first dose of the ACTH peptide preparation comprises a first dose of between about 10 IU and about 150 IU, and the one or more subsequent doses of the ACTH peptide preparation are between about 20%-60% of the first dose.

12. The method of claim 1, wherein the first dose and the one or more subsequent doses of the ACTH peptide preparation comprises a first dose of between about 10 IU and about 150 IU, and the one or more subsequent doses of the ACTH peptide preparation are between about 10 IU and about 80 IU, the first dose and the one or more subsequent doses of the ACTH peptide preparation are intermittent.

13. A method of treating renal damage caused by ischemia to the kidney in an individual in need thereof comprising administering to the individual in need thereof an adrenocorticotropic hormone (ACTH) as an ACTH peptide preparation having about 90% or greater homology with full length porcine ACTH, wherein the ACTH preparation is administered as a first dose and one or more subsequent doses.

* * * * *

SEQUENCE LISTING

```
<160> NUMBER OF SEQ ID NOS: 7

<210> SEQ ID NO 1
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ser Tyr Ser Met Glu His Phe Arg Trp Gly Lys Pro Val Gly Lys Lys
1               5                   10                  15

Arg Arg Pro Val Lys Val Tyr Pro Asp Gly Ala Glu Asp Gln Leu Ala
            20                  25                  30

Glu Ala Phe Pro Leu Glu Phe
        35

<210> SEQ ID NO 2
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Tyr Ser Met Glu His Phe Arg Trp Gly Lys Pro Val Gly Lys Lys
1               5                   10                  15

Arg Arg Pro Val Lys Val Tyr Pro
            20

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 3

Ser Tyr Ser Met Glu His Phe Arg Trp Gly Lys Pro Val Gly Lys Lys
1               5                   10                  15

Arg

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Glu His Phe Arg Trp Gly
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: D-Lys

<400> SEQUENCE: 5

Met Glu His Phe Lys Phe
1               5

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Tyr Ser Met Glu His Phe Arg Trp Gly Lys Pro Val
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala

<400> SEQUENCE: 7

Ala Gln Tyr Phe Arg Trp Gly
1               5
```